(12) United States Patent
Usami et al.

(10) Patent No.: US 7,396,977 B2
(45) Date of Patent: Jul. 8, 2008

(54) METHOD OF ELEVATING PHOTOSYNTHESIS SPEED OF PLANT BY IMPROVING PYRUVATE PHOSPHATE DIKINASE

(75) Inventors: Satoru Usami, Shizuoka (JP); Shozo Ohta, Kanagawa (JP); Yuji Ishida, Shizuoka (JP)

(73) Assignee: Japan Tobacco Inc., Tokyo (JP)

( * ) Notice: Subject to any disclaimer, the term of this patent is extended or adjusted under 35 U.S.C. 154(b) by 93 days.

(21) Appl. No.: 10/493,537

(22) PCT Filed: Oct. 23, 2002

(86) PCT No.: PCT/JP02/10993

§ 371 (c)(1),
(2), (4) Date: Apr. 22, 2004

(87) PCT Pub. No.: WO03/035875

PCT Pub. Date: May 1, 2003

(65) Prior Publication Data

US 2006/0064783 A1 Mar. 23, 2006

(30) Foreign Application Priority Data

Oct. 23, 2001 (JP) .............................. 2001-324899

(51) Int. Cl.
*C12N 15/82* (2006.01)
(52) U.S. Cl. ...................................... 800/278; 435/468
(58) Field of Classification Search ........................ None
See application file for complete search history.

(56) References Cited

U.S. PATENT DOCUMENTS 5,891,726 A * 4/1999 Sheriff ........................ 435/419
5,912,156 A   6/1999 Ohta et al.

FOREIGN PATENT DOCUMENTS

| EP | 0 690 128 A1 | 1/1996 |
| EP | 0690128 A1 * | 1/1996 |
| EP | 0 874 056 A1 | 10/1998 |
| JP | 07-184657 A | 7/1995 |
| JP | 09-065886 A | 3/1997 |
| JP | 11-341928 A | 12/1999 |

OTHER PUBLICATIONS

Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Rosche et al. (GenBank, NCBI, Sequenc Accession No. X79192, pp. 1-7, Published Sep. 1998).*
Ishida et al. (Nature Biotechnology 14:745-750, 1996).*
Ohta et al. (FEBS Letters, 396:152-156, 1996).*
Rosche et al. (GenBank, NCBI, Sequence Accession No. X79095, pp. 1-9, Published Apr. 1996).*
Burnell (Plant Cell Physiol., 31:295-297, 1990).*
Jeanneau et al. (Biochimie, 84:1127-1135, Nov. 2002).*
James N. Burnell, *Plant Cell Physiol.*, vol. 31, No. 2, (1990), pp. 295-297.
S. Usami et al., *Plant Molecular Biology*, vol. 27, (1995), pp. 969-980.
Shozo Ohta et al., *FEBS Letters*, vol. 396, (1996), pp. 152-156.
Carlotta A Glackin et al., *Proc. Natl. Acad. Sci.*, vol. 87, (Apr. 1990), pp. 3004-3008.
Makoto Matsuoka, *The Journal of Biological Chemistry*, vol. 265, No. 28, (Oct. 5, 1990), pp. 16772-16777.
Shozo Ohta et al., *Plant Cell Physiol.*, vol. 31, No. 6, (1990), pp. 805-813.
Jun Ueki et al., *Plant Cell Physiol.*, vol. 36, No. 5, (1995), pp. 903-914.
Alan H. Christensen et al., *Plant Molecular Biology*, vol. 18, (1992), pp. 675-689.
Vimla Vasil et al., *Plant Physiol.*, vol. 91, (1989), pp. 1575-1579.
Jun Ueki et al., *Plant Cell Physiol.*, vol. 40, No. 6, (1999), pp. 618-623.
Makoto Matsuoka et al., *Proc. Natl. Acad. Sci.*, vol. 90, (Oct. 1993), pp. 9586-9590.
Shuichi Yanagisawa et al., *J. Biochem.*, vol. 106, (1989), pp. 982-987.
Makoto Matsuoka et al., *The Plant Journal*, vol. 6, No. 3, (1994), pp. 311-319.
Ming-Bo Wang et al., *Plant Molecular Biology Reporter*, vol. 15, (1997), pp. 209-215.
Maurice S.B. Ku et al., *Nature Biotechnology*, vol. 17, (Jan. 1999), pp. 76-80.
Significant Accumulation of $C_4$-Specific Pyruvate, Orthophosphate Dikinson in a $C_3$ Plant, Rice[1]; Hiroshi Fukayama, et al.; Plant Physiology, Nov. 2001, vol. 127, pp. 1136-1146.

* cited by examiner

*Primary Examiner*—Phuong T. Bui
*Assistant Examiner*—Vinod Kumar
(74) *Attorney, Agent, or Firm*—Birch, Stewart, Kolasch & Birch, LLP

(57) ABSTRACT

The present invention relates to the transformation of C4 plants. It also relates to the high-level expression of foreign genes in C4 plants. More specifically, the present invention relates to the creation of C4 plants retaining an excellent photosynthetic capacity at low temperature by achieving high-level expression of an enzyme constituting the C4 photosynthetic pathway. In the present invention, C4 plants are transformed using an expression cassette that comprises a promoter, a C4 plant genomic gene, under control of said promoter, encoding an enzyme constituting a photosynthetic pathway, and a terminator. The C4 plant genomic gene encoding an enzyme constituting a photosynthetic pathway is preferably a C4 plant genome-derived PPDK gene or a modified form thereof. The present invention is particularly useful in improving the production of C4 plants having PPDK (especially, in improving the production of maize under low temperature conditions).

4 Claims, 8 Drawing Sheets

Figure 5A

Maize PPDK amino acid sequence (C-terminal 1/6 region being boxed)

```
MTASVSRAICVQKPGSKCTRDREATSFARRSVAAPRPPHAKAAGVIRSDSGAGRGQHCSPLRAVVDAAP
IQTTKKRVFHFGKGKSEGNKTMKELLGGKGANLAEMASIGLSVPPGFTVSTEACQQYQDAGCALPAGLW
AEIVDGLQWVEEYMGATLGDPQRPLLLSVRSGAAVSMPGMMDTVLNLGLNDEVAAGLAAKSGERFAYDS
FRRFLDMFGNVVMDIPRSLFEEKLEHMKESKGLKNDTDLTASDLKELVGQYKEVYLSAKGEPFPSDPKK
QLELAVLAVFNSWESPRAKKYRSINQITGLRGTAVNVQCMVFGNMGNTSGTGVLFTRNPNTGEKKLYGE
FLVNAQGEDVVAGIRTPEDLDAMKNLMPQAYDELVENCNILESHYKEMQDIEFTVQENRLWMLQCRTGK
RTGKSAVKIAVDMVNEGLVEPRSAIKMVEPGHLDQLLHPQFENPSAYKDQVIATGLPASPGAAVGQVVF
TAEDAEAWHSQGKAAILVRAETSPEDVGGMHAAVGILTERGGMTSHAAVVARGWGKCCVSGCSGIRVND
AEKLVTIGGHVLREGEWLSLNGSTGEVILGKQPLSPPALSGDLGTFMAWVDDVRKLKVLANADTPDDAL
TARNNGAQGIGLCRTEHMFFASDERIKAVRQMIMAPTLELRQQALDRLLPYQRSDFEGIFRAMDGLPVT
IRLLDPPLHEFLPEGNIEDIVSELCAETGANQEDALARIEKLSEVNPMLGFRGCRLGISYPELTEMQAR
AIFEAAIAMTNQGVQVFPEIMVPLVGTPQELGHQVTLIRQVAEKVFANVGKTIGYKVGTMIEIP|RAALV|
|ADEIAEQAEFFSFGTNDLTQMTFGYSRDDVGKFIPVYLAQGILQHDPFEVLDQRGVGELVKLATERGRK|
|ARPNLKVGICGEHGGEPSSVAFFAKAGLDYVSCSPFRVPIARLAAAQVLV|
```

Figure 5B

*Flaveria brownii* PPDK amino acid sequence (C-terminal 1/6 region being boxed)

```
MSSLFVEGMPLKSANESCLPASVKQRRTGDLRRLNHHRQPAFVRGICRRKLSGVSRIELRTGGLTLPRA
VLNPVSPPVTTTKKRVFTFGKGNSEGNKDMKSLLGGKGANLAEMASIGLSVPPGLTISTEACEEYQQNG
KKLPPGLWDEILEGLQYVQKEMSASLGDPSKALLLSVRSGAAISMPGMMDTVLNLGLNDEVVDGLAAKS
GARFAYDSYRRFLDMFGNVVMGIPHSLFDEKLEQMKAEKGIHLDTDLTAADLKDLAEQYKNVYVEAKGE
KFPTDPKKQLELAVNAVFDSWDSPRANKYRSINQITGLKGTAVNIQCMVFGNMGNTSGTGVLFTRNPST
GEKKLYGEFLVNAQGEDVVAGIRTPEDLVTMETCMPEAYRELVENCVILERHYKDMMDIEFTVQENRLW
MLQCRTGKRTGKGAVRIAVDMVNEGLIDTRTAIKRVETQHLDQLLHPQFENPSAYKSHVVATGLPASPG
AAVGQVVFSAEDAETWHAQGKSAILVRTETSPEDVGGMHAAAGILTARGGMTSHAAVVARGWGKCCVSG
CADIRVNDDMKVFTIGDRVIKEGDWLSLNGSTGEVILGKQLLAPPAMSNDLETFMSWADQARRLKVMAN
ADTPNDALTARNNGAQGIGLCRTEHMFFASDERIKAVRKMIMAVTPEQRKAALDLLLPYQRSDFEGIFR
AMDGLPVTIRLLDPPLHEFLPEGDLEHIVNELTADTGMSKDEIYSRIEKLSEVNPMLGFRGCRLGISYP
ELTEMQVRAIFQAAVSMNNQGVTVIPEIMVPLVGTPQELRHQIGVIRGVAANVFAEMGLTLEYKVGTMI
EIP|RAALIADEIAKEAEFFSFGTNDLTQMTFGYSRDDVGKFLPIYLSQGILQHDPFEVLDQKGVGQLIK|
|MATEKGRAANPNLKVGICGEHGGEPSSVAFFDGVGLDYVSCSPFRVPIARLAAAQVVV|
```

Figure 5C

Comparison of C-terminal 1/6 region between these amino acid sequences
(different residues being boxed)

```
RAAL|V|ADEIA|EQ|AEFFSFGTNDLTQMTFGYSRDDVGKF|I|P|V|YL|A|QGILQHDPFEVLDQ|R|GVGE|L|VK|L|ATE
RAAL|I|ADEIA|KE|AEFFSFGTNDLTQMTFGYSRDDVGKF|L|P|I|YL|S|QGILQHDPFEVLDQ|K|GVGQ|L|IK|M|ATE

|R|GR|K|A|R|PNLKVGICGEHGGEPSSVAFF|AKA|GLDYVSCSPFRVPIARLAAAQV|L|V
|K|GR|A|A|N|PNLKVGICGEHGGEPSSVAFF|DGV|GLDYVSCSPFRVPIARLAAAQV|V|V
```

METHOD OF ELEVATING PHOTOSYNTHESIS SPEED OF PLANT BY IMPROVING PYRUVATE PHOSPHATE DIKINASE

FIELD OF THE INVENTION

The present invention relates to the transformation of C4 plants. It also relates to the high-level expression of foreign genes in C4 plants. More specifically, the present invention relates to the creation of C4 plants retaining an excellent photosynthetic capacity at low temperature by achieving high-level expression of an enzyme constituting the C4 photosynthetic pathway. The present invention is particularly useful in improving the production of C4 plants having PPDK (especially, in improving the production of maize under low temperature conditions).

BACKGROUND OF THE INVENTION

Plant pyruvate, orthophosphate dikinase (PPDK; EC2.7.9.1) is one of the important enzymes constituting the C4 cycle and it has been believed that there is a high correlation between PPDK activity and photosynthesis rate in C4 plants. Further, PPDK has the lowest activity among enzymes constituting the C4 cycle; the PPDK reaction has been regarded as a rate-limiting stage of C4 photosynthesis. Also, PPDK is a tetramer composed of four subunits which are weakly associated with each other. When exposed to low temperature conditions (at or below 12° C.), PPDK is known to be dissociated into dimers or monomers, thus rapidly losing its activity. In general, maize PPDK will lose approximately 70% of its activity when treated at 0° C. for 20 minutes. Meanwhile, the activity of maize PPDK was measured at various temperatures to prepare an Arrhenius plot, indicating that there was an inflection point at 11.7° C., which was found to match the critical temperature for maize growth. In view of these points, a decrease in PPDK activity has been regarded as the main factor responsible for slowdown of photosynthesis in C4 plants at low temperature.

*Flaveria brownii* (*F. brownii*), an Asteraceae plant, is categorized as a C3/C4 intermediate type and its PPDK is known to be hardly deactivated even when treated at a temperature as low as 0° C. (Burnell J N, A comparative sturdy of the cold-sensitivity of pyruvate, Pi dikinese in *Flaveria* species, Plant Cell Physiol., 31:295-297 (1990)). Hence, it was expected that this cold-tolerant PPDK gene could be used to create C4 plants capable of C4 photosynthesis at a lower temperature, i.e., C4 plants more resistant to cold.

In the previous studies, the inventors of the present invention succeeded in determining a region important for cold tolerance of PPDK by isolation and DNA sequencing of the *F. brownii* PPDK gene. They also demonstrated that the sequence of this region could be used to convert cold-sensitive PPDK into a cold-tolerant form through recombination between this sequence and the DNA of cold-sensitive PPDK derived from other plant (WO95/15385; Usami S, Ohta S, Komari T, Burnell J N, Cold stability of pyruvate, orthophosphate dikinase of *Flaveria brownii*, Plant Mol Biol, 27:969-80 (1995); Ohta S, Usami S, Ueki J, Kumashiro T, Komari T, Burnell J N, Identification of the amino acid residues responsible for cold tolerance in *Flaveria brownii* pyruvate, orthophosphate dikinase, FEBS Lett, 396:152-6 (1996)).

Through many studies of maize transformants, however, the inventors of the present invention found that effects of the artificially introduced PPDK (introduced PPDK) were masked by naturally-occurring PPDK in C4 plants (endogenous PPDK). This would be attributed to an abundance of endogenous PPDK constituting several percent of soluble proteins in C4 plants. Further, the inventors of the present invention found that heterotetramers could be formed between introduced PPDK subunits and endogenous PPDK subunits.

To overcome the phenomenon where effects of the introduced PPDK are masked by the endogenous PPDK, two techniques are available, one of which involves increasing the expression level of the introduced PPDK and the other is inhibition of the endogenous PPDK. The former involves integrating a sequence (e.g., intron) into a gene construct for transformation (in most cases, an intron(s) being integrated between a promoter and a structural gene) to increase the expression level of an externally introduced gene (WO96/30510: PLD intron, WO97/47755: double-ligated introns). The latter is an antisense technique for inhibiting the expression level of an object gene by introduction of a gene whose mRNA has a sequence complementary to mRNA from the object gene to be inhibited from expression (Japanese Patent No. 2651442 and its divisional patent No. 2694924). The inventors of the present invention have tried these techniques.

In increasing the expression level of the introduced PPDK by integration of an intron(s) etc., a gene construct used for transformation was constructed in a general manner through ligation between a maize PPDK promoter (Glackin Calif., Grula J W, Organ-specific transcripts of different size and abundance derive from the same pyruvate, orthophosphate dikinase gene in maize, PNAS, 87:3004-3008 (1990)) and a cDNA molecule of the PPDK gene derived from *F. brownii*, *F. bidentis* (Usami S, Ohta S, Komari T, Burnell J N, Cold stability of pyruvate, orthophosphate dikinase of *Flaveria brownii*, Plant Mol Biol, 27:969-80 (1995)) or maize (Matsuoka M, Structure, genetic mapping, and expression of the gene for pyruvate, orthophosphate dikinase from maize, J. Biol. Chem, 265:16772-16777 (1990)). At the same time, the inventors of the present invention attempted to increase the expression level of the introduced PPDK by inserting any one of the following introns between the promoter and the structural gene: Intron 1 of the Castor bean catalase gene (Ohta S, Mita S, Hattori T, Nakamura K, Construction and expression in tobacco of a β-glucuronidase (GUS) reporter gene containing an intron within the coding sequence, Plant Cell Physiol, 31:805-813 (1990)), Intron 1 of the rice phospholipase D gene (Ueki J, Morioka S, Komari T, Kumashiro T, Purification and characterization of phospholipase D from rice and maize (*Zea mays* L.), Plant Cell Physiol, 36:903-914 (1995)), Intron 1 of maize ubiquitin (Christensen et al., (1992)) and Intron 1 of maize Shrunken-1 (Vasil V, Clancy M, Ferl R J, Vasil I K, Hannah L C, Increased gene expression by the first intron of maize Shrunken-1 locus in grass species, Plant Physiol, 91:1575-1579 (1989)). Further, based upon a report suggesting that repeated introns resulted in an increased expression level (Ueki J, Ohta S, Morioka S, Komari T, Kuwata S, Kubo T, Imaseki H, The synergistic effects of two-intron insertions on heterologous gene expression and advantages of the first intron of a rice gene for phospholipase D, Plant Cell Physiol, 40:618-623 (1999)), the inventors of the present invention also attempted to insert multiple repeated introns.

DISCLOSURE OF THE INVENTION

The studies of the present inventors indicated that these introns resulted in an increased expression level in the order: Intron 1 of Shrunken-1<Intron 1 of the Castor bean catalase gene<Intron 1 of the rice phospholipase D gene and that these introns, when inserted in combination, resulted in a greater increase in expression level than when inserted alone, for example, Intron 1 of the rice phospholipase D gene resulted in an increased expression level when combined with Intron 1 of the Castor bean catalase gene or Intron 1 of maize ubiquitin.

However, even the most improved transformants expressed the introduced PPDK at a level as low as around 700 μg/g of fresh green leaves, which was only about half that of the endogenous PPDK; there was no remarkable effect resulting from the introduced PPDK. Although the expression level of the introduced PPDK is regarded as high compared to other artificially introduced genes, it would be impossible to clarify effects of the introduced gene in a case where there are abundant products of the endogenous gene (i.e., where the endogenous gene is highly expressed) unless the endogenous gene is inhibited.

In contrast, an antisense gene for inhibition of the endogenous PPDK was constructed based on a 395 bp sequence of the maize PPDK gene covering from SacI in the 5'-untranslated region to EcoRI in Intron 1, 6 repeated copies of this sequence, or a cDNA-derived PstI fragment (2.4 kb) covering almost all segments of the maize PPDK mature enzyme. The constructed antisense gene was used to transform maize. The reason why attention was directed to the 395 bp sequence was because this sequence corresponded to a transit peptide segment, for which low homology was shared between maize PPDK and F. brownii PPDK, and hence it would be able to selectively inhibit the maize PPDK alone.

As a consequence, there was no inhibitory effect on expression levels was observed in simple introduction of the antisense gene for the 395 bp sequence. With low frequency, some transformants modified to inhibit their endogenous PPDK appeared in a case where maize was transformed with an antisense gene for the 6 repeated copies of the 395 bp sequence or the cDNA-derived PstI fragment (2.4 kb). However, such transformants modified to inhibit their endogenous PPDK also had a reduced level of the introduced PPDK and therefore did not achieve specific inhibition of the endogenous PPDK alone. Further, such transformants were too weak to grow and most of them withered and died before maturation because inhibition occurred on PPDK essential for C4 plants, including both the endogenous PPDK and the introduced PPDK. Also, no seed production was seen in even those transformants that came into flower. It was theoretically impossible to selectively control the expression of genes sharing a very similar sequence by the antisense technique in view of its mechanism, thus indicating that such a technique could not be adapted in this case.

There is an attempt to introduce a genomic gene instead of cDNA to achieve high-level expression, in C3 plants, of a gene for an enzyme constituting the C4 photosynthetic pathway (JP 10-248419 A). In this attempt, however, a gene that is not present in C3 plants (or, if any, expressed at a very low level) is merely introduced from C4 plants. It would be much more difficult to achieve further expression, in C4 plants, of genes naturally occurring in C4 plants or high-level expression, in C4 plants, of genes encoding proteins which are already expressed in abundance in C4 plants, like photosynthesis-related enzymes, than to achieve expression of C4 plants-derived genes in C3 plants.

A variety of previous biochemical studies have estimated that PPDK might be a rate-limiting factor of C4 photosynthesis. However, no conclusive evidence has been established that these previous studies were correct because there was no report showing actual high-level expression of PPDK in C4 plants or artificial introduction of PPDK with new properties.

As stated above, the cDNA-based technique could not increase expression of the introduced gene to a sufficient level even in combination with an intron(s) etc., while the antisense technique was unable to selectively inhibit the endogenous gene alone. For this reason, the inventors of the present invention tried to introduce a genomic gene.

Meanwhile, the studies of the present inventors indicated that when a cold-tolerant F. brownii PPDK cDNA was introduced as such into maize, the introduced gene was expressed at a very low level. This would be because F. brownii is a C3/C4 intermediate plant and inherently produces a smaller amount of PPDK than C4 plants. Further, the inventors of the present invention have found that expression of F. brownii PPDK in C4 plants was improved by constructing a chimeric gene between a pure C4 plant F. bidentis or maize and F. brownii.

In turn, the inventors of the present invention made a variety of studies on genomic gene introduction based on the maize PPDK genomic gene, instead of the genomic gene for C3/C4 intermediate F. brownii PPDK. As a result, they found that the expression level of PPDK in maize was increased by simple introduction of the maize PPDK genomic gene into maize and that the expression level of maize PPDK under cold cultivation was increased using a gene that was modified into a cold-tolerant type by mutagenesis in a certain region of the maize PPDK genomic gene. These findings led to the completion of the present invention.

The present invention provides a method for increasing the expression level of an enzyme constituting a photosynthetic pathway in a C4 plant, comprising transforming the C4 plant using an expression cassette that comprises a promoter, a C4 plant genomic gene, under control of said promoter, encoding the enzyme, and a terminator. It also provides a transgenic C4 plant obtainable by the method.

BRIEF DESCRIPTION OF THE DRAWINGS

FIG. 5A shows the maize PPDK amino acid sequence (SEQ ID NO: 17) FIG. 5B shows the F. brownii PPDK amino acid sequence (SEQ ID NO: 18). The line-encircled amino acid sequence is an approximately ⅙ region from the C-terminal, which is important for cold tolerance.

FIG. 5C shows a comparison of the C-terminal ⅙ region between maize PPDK (residues 824-947 of SEQ ID NO: 17) and *F. brownii* PPDK (residues 833-955 of SEQ ID NO: 18) amino acid sequences. The line-encircled amino acid residues are different between them.

DETAILED DESCRIPTION OF THE INVENTION

Figure 1:
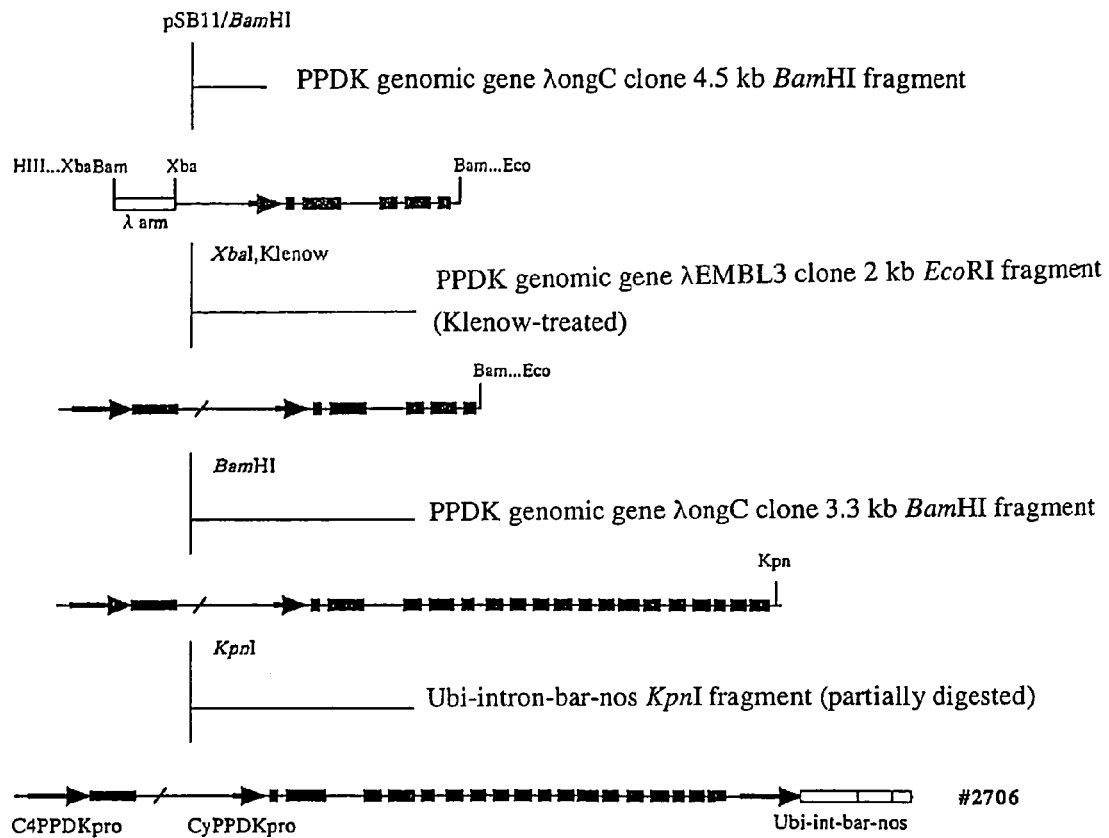
FIG. 1 shows procedures for construction of #2706 in Example 1.

Various types of enzymes are known to be included in the "enzyme constituting the C4 photosynthetic pathway" as used herein. Among these enzymes, the method of the present invention can be used to increase the expression levels of enzymes that are expressed at relatively low levels, easily deactivated, and/or involved in the rate-limiting stage of the photosynthetic pathway. In particular, the method of the present invention can be used to increase the expression levels of enzymes that have the properties as mentioned above under low temperature conditions (e.g., at or below about 12° C.). PPDK is known as an example of such enzymes. Also, the method of the present invention can be used to enhance the photosynthetic capacity at low temperature in C4 plants having a limit for growth under low temperature conditions (e.g., at or below about 12° C.).

In a case where the method of the present invention is used to create transgenic C4 plants, a gene consisting of any one of the following DNA molecules may be used as a "C4 plant genomic gene encoding an enzyme constituting a photosynthetic pathway." The method using such a gene is particularly preferred to obtain maize plants modified to enhance their photosynthesis rate under low temperature conditions:

(a) the maize PPDK genomic gene, i.e., a DNA molecule consisting of the nucleotide sequence of Nos. 1732-8508 of SEQ ID NO: 15;

(b) a DNA molecule consisting of a nucleotide sequence derived from the nucleotide sequence of Nos. 1732-8508 of SEQ ID NO: 15 by deletion, substitution, addition or insertion of one or more nucleotides, and encoding a protein possessing PPDK activity;

(c) a DNA molecule being hybridizable under stringent conditions to the DNA molecule being complementary to the DNA molecule consisting of the nucleotide sequence of Nos. 1732-8508 of SEQ ID NO: 15, and encoding a protein possessing PPDK activity; and (d) a DNA molecule consisting of a nucleotide sequence being at least 50% (preferably at least 60%, more preferably at least 70%, even more preferably at least 80%, still more preferably at least 90%, particularly preferably at least 95%, and most preferably at least 98%) homologous to the nucleotide sequence of Nos. 1732-8508 of SEQ ID NO: 15, and encoding a protein possessing PPDK activity. To calculate a homology between nucleotide sequences, a commercially available software package may be used. As used herein, the term "stringent conditions" refers to hybridization conditions of a temperature of at least about 40° C., a salt concentration of about 6×SSC (1×SSC=15 mM sodium citrate buffer; pH 7.0; 0.15 M sodium chloride) and 0.1% SDS, preferably at least about 50° C., more preferably at least about 65° C.

Alternatively, a gene encoding any one of the following proteins may be used:

(a) a protein consisting of the amino acid sequence of SEQ ID NO: 17;

(b) a protein consisting of an amino acid sequence derived from the amino acid sequence of SEQ ID NO: 17 by deletion, substitution, addition or insertion of one or more amino acids, and possessing PPDK activity;

(c) PPDK derived from a C4 plant; and (d) a protein consisting of an amino acid sequence being at least 50% (preferably at least 60%, more preferably at least 70%, even more preferably at least 80%, still more preferably at least 90%, particularly preferably at least 95%, and most preferably at least 98%) homologous to the amino acid sequence of SEQ ID NO: 17, and possessing PPDK activity. The term "homology" when used herein for amino acid sequences generally means that the extent of the similarity between amino acid residues constituting the respective sequences to be compared. In this sense, the presence of gaps and the nature of amino acids are taken into account. To calculate a homology, a commercially available software package may be used.

As used herein, the term "genomic gene" encompasses a genome-derived gene per se and a modified form thereof, unless otherwise specified. Also as used herein, the term "C4 plant genomic gene encoding an enzyme constituting a photosynthetic pathway" encompasses a C4 plant genome-derived gene per se and a modified form thereof. Such a modified gene is preferably modified to have one or more nucleotide substitutions such that the amino acid sequence of the enzyme encoded by the gene is equivalent to the amino acid sequence of the corresponding enzyme in plants with desired characteristics (e.g., cold tolerance), preferably in C4 plants or plants of an intermediate nature between C3 and C4, more preferably in plants belonging to *Flaveria*, even more preferably in *F. brownii* or *F. bidentis*. Preferably, such a substitution is allowed to occur exclusively in exon segments, with as many intron segments as possible being retained intact. The number of bases to be substituted is not particularly limited, but it is preferably about 1 to 50, more preferably about 1 to 40, and most preferably about 1 to 30 (e.g., 29) when the enzyme constituting a photosynthetic pathway is PPDK. Likewise, the number of amino acids to be substituted is preferably about 1 to 40, more preferably about 1 to 30, and most preferably about 1 to 20 (e.g., 17 as shown in FIG. 5) when the enzyme constituting a photosynthetic pathway is PPDK.

In one preferred embodiment of the present invention for creation of cold-tolerant C4 plants, a PPDK gene that is modified into a cold-tolerant type and capable of high-level expression in target plants is used as a C4 plant genomic gene encoding an enzyme constituting a photosynthetic pathway.

Such a modification into a cold-tolerant type is accomplished, for example, by establishing "equivalence" between the amino acid sequence of PPDK to be expressed and the corresponding PPDK amino acid sequence found in plants expressing cold-tolerant PPDK (preferably at a high level). Specifically, this modification is accomplished, e.g., by introducing a mutation(s) such that the amino acid sequence is equivalent to *F. brownii* PPDK. More specifically, it is accomplished, for example, by introducing 17 point mutations into or downstream of Exon 15 of the maize PPDK genome-derived gene such that an amino acid sequence covering an approximately ⅙ region from the C-terminal of the maize PPDK (said amino acid sequence corresponding to the sequence downstream of No. 7682 in SEQ ID NO: 15) is identical with an amino acid sequence covering an approximately ⅙ region from the C-terminal of *F. brownii* PPDK, which is important for cold tolerance (said amino acid sequence corresponding to the sequence downstream of No. 7682 in SEQ ID NO: 16). For this purpose, it is desirable to use codons that occur frequently in maize. Introduction of point mutations may be carried out in a general manner well known to those skilled in the art, e.g., by PCR using a primer set(s) carrying mutations.

When used herein for amino acid sequences, the term "equivalent" or "equivalence" encompasses both the meanings that an amino acid sequence is "identical" with a target sequence and that an amino acid sequence is modified to include substitution of amino acids by other qualitatively similar amino acids, with consideration given to the nature of amino acids. Likewise, for the case where the amino acid sequence of a certain enzyme is "equivalent to the amino acid sequence of the corresponding enzyme in plants with desired characteristics," the meaning is that the former amino acid sequence is exactly identical with the latter amino acid sequence, and that the former amino acid sequence is not exactly identical with the latter amino acid sequence, but is modified to include substitution of one or more (preferably about 1 to 40, more preferably about 1 to 30, most preferably about 1 to 20) amino acids different from those of the latter amino acid sequence so as to establish equivalence.

To obtain a PPDK gene modified into a cold-tolerant type and capable of high-level expression in target plants, for example, the above-mentioned mutations are allowed to occur exclusively in exon segments, with as many intron segments of the C4 plant genome-derived PPDK gene as possible being retained intact.

As a mutated "C4 plant genomic gene encoding an enzyme constituting a photosynthetic pathway," a gene consisting of any one of the following DNA molecules may be used. Such a gene is particularly preferred to obtain maize plants modified to enhance their photosynthetic rate under low temperature conditions:

(a) a nucleotide sequence derived from the region downstream of Exon 15 of the maize PPDK genomic gene, whose amino acid sequence is mutated to be equivalent to the *F. brownii* PPDK amino acid sequence, i.e., a DNA molecule consisting of the nucleotide sequence of Nos. 1732-8508 of SEQ ID NO: 16;

(b) a DNA molecule consisting of a nucleotide sequence derived from the nucleotide sequence of Nos. 1732-8508 of SEQ ID NO: 16 by deletion, substitution, addition or insertion of one or more nucleotides, and encoding a protein possessing PPDK activity;

(c) a DNA molecule being hybridizable under stringent conditions to the DNA molecule being complementary to the DNA molecule consisting of the nucleotide sequence of Nos. 1732-8508 of SEQ ID NO: 16, and encoding a protein possessing PPDK activity; and (d) a DNA molecule consisting of a nucleotide sequence being at least 50% (preferably at least 60%, more preferably at least 70%, even more preferably at least 80%, still more preferably at least 90%, particularly preferably at least 95%, and most preferably at least 98%) homologous to the nucleotide sequence of Nos. 1732-8508 of SEQ ID NO: 16, and encoding a protein possessing PPDK activity.

Alternatively, a gene encoding any one of the following proteins may be used:

(a) *F. brownii* PPDK, i.e., a protein consisting of the amino acid sequence of SEQ ID NO: 18;

(b) a protein consisting of an amino acid sequence derived from the amino acid sequence of SEQ ID NO: 18 by deletion, substitution, addition or insertion of one or more amino acids, and possessing PPDK activity;

(c) PPDK derived from a C4 plant being cold-tolerant, or PPDK derived from a C3/C4 intermediate plant being cold-tolerant (preferably *Flaveria brownii*); and (d) a protein consisting of an amino acid sequence being at least 50% (preferably at least 60%, more preferably at least 70%, even more preferably at least 80%, still more preferably at least 90%, particularly preferably at least 95%, and most preferably at least 98%) homologous to the amino acid sequence of SEQ ID NO: 18, and possessing PPDK activity.

The present invention also provides an expression cassette that comprises an expression control region such as a promoter, a downstream C4 plant genomic gene (either of the genome-derived type or the modified type), under control of said region, encoding an enzyme constituting a photosynthetic pathway, and a terminator.

Any promoter may be used in the expression cassette of the present invention as long as it is operable in plants to be transformed. Examples of a promoter available for use include promoters driving high-level expression, in green organs, of photosynthesis-related genes including PPDK (Matsuoka et al., Proc Natl Acad Sci USA, 90:9586-9590 (1993)), PEPC (Yanagisawa and Izui, J Biochem, 106:982-987 (1989) and Matsuoka et al., Plant J, 6:311-319 (1994)) and Rubisco (Matsuoka et al., Plant J, 6:311-319 (1994)); cauliflower mosaic virus 35S promoter; ubiquitin promoter (Cornejo et al., Plant Mol Biol, 23:567-581 (1993)); actin promote (McElroy et al., Plant Cell, 2:163-171 (1990)); α-tubulin promoter (Carpenter et al., Plant Mol Biol, 21:937-942 (1993)); Sc promoter (Schenk et al., Plant Mol Biol, 39:1221-1230 (1999)); pea PAL promoter; Prp1 promoter (JP 10-500312 A); hsr203J promoter (Pontier et al., Plant J, 5:507-521 (1994)); EAS4 promoter (Yin et al., Plant Physiol, 115:437-451 (1997)); PR1b1 promoter (Tornero et al., Mol Plant Microbe Interact, 10:624-634 (1997)); tap1 promoter (Mohan et al., Plant Mol Biol, 22:475-490 (1993)); and AoPR1 promoter (Warner et al., Plant J, 3:191-201 (1993)).

Any terminator may be used in the expression cassette of the present invention as long as it is operable in plants to be transformed. Examples of a terminator available for use include nos terminator, CaMV 35S terminator, gene7 terminator and protease inhibitor II terminator.

Expression cassettes comprising the following DNA molecules may be presented by way of example for the expression cassette of the present invention:

(a) a DNA molecule consisting of the nucleotide sequence of SEQ ID NO: 15;

(b) a DNA molecule consisting of a nucleotide sequence derived from the nucleotide sequence of SEQ ID NO: 15 by deletion, substitution, addition or insertion of one or more nucleotides, and encoding a protein possessing PPDK activity;

(c) a DNA molecule being hybridizable under stringent conditions to the DNA molecule being complementary to the DNA molecule consisting of the nucleotide sequence of SEQ ID NO: 15, and encoding a protein possessing PPDK activity; and (d) a DNA molecule consisting of a nucleotide sequence being at least 50% (preferably at least 60%, more preferably at least 70%, even more preferably at least 80%, still more preferably at least 90%, particularly preferably at least 95%, and most preferably at least 98%) homologous to the nucleotide sequence of SEQ ID NO: 15, and encoding a protein possessing PPDK activity; or (a) a DNA molecule consisting of the nucleotide sequence of SEQ ID NO: 16;

(b) a DNA molecule consisting of a nucleotide sequence derived from the nucleotide sequence of SEQ ID NO: 16 by deletion, substitution, addition or insertion of one or more nucleotides, and encoding a protein possessing PPDK activity;

(c) a DNA molecule being hybridizable under stringent conditions to the DNA molecule complementary to the DNA molecule consisting of the nucleotide sequence of SEQ ID NO: 16, and encoding a protein possessing PPDK activity; and (d) a DNA molecule consisting of a nucleotide sequence being at least 50% (preferably at least 60%, more preferably at least 70%, even more preferably at least 80%, still more preferably at least 90%, particularly preferably at least 95%, and most preferably at least 98%) homologous to the nucleotide sequence of SEQ ID NO: 16, and encoding a protein possessing PPDK activity.

The expression cassette of the present invention is particularly useful in creating C4 plants modified to enhance their photosynthesis rate under low temperature conditions. The present invention also provides a recombinant vector containing such an expression cassette.

A vector used for subcloning of each DNA fragment constituting the expression cassette of the present invention may be conveniently prepared by ligating a desired gene to a recombination vector (plasmid DNA) available in the art in a general manner. Specific examples of a vector available for use include pCR2.1, pBluescript, pUC18, pUC19 and pBR322, by way of example for E. coli-derived plasmids.

A plant transformation vector is useful in introducing the expression cassette of the present invention into target plants. Any plant transformation vector may be used as long as it is capable of expressing the gene of interest in plant cells and thus producing the protein of interest. Examples include pBI221, pBI121 (both available form Clontech) and vectors derived therefrom. In particular, for transformation of monocotyledonous plants, the following vectors may be exemplified: pIG121Hm, pTOK233 (both found in Hiei et al., Plant J., 6:271-282 (1994)), pSB424 (Komari et al., Plant J., 10:165-174 (1996)), pSB11, pSB21 and vectors derived therefrom.

Preferably, a plant transformation vector at least comprises a promoter, an initiation codon, a C4 plant genomic gene (either of the genome-derived type or the modified type) encoding an enzyme constituting a photosynthetic pathway, a termination codon and a terminator. It may also comprise, as appropriate, a DNA sequence encoding a signal peptide, an enhancer sequence, 5'- and 3'-untranslated regions of the desired gene, a selective marker region and the like. Examples of a marker gene include genes resistant to antibiotics such as tetracycline, ampicillin, kanamycin, neomycin, hygromycin and spectinomycin, as well as luciferase gene, β-galactosidase gene, β-glucuronidase (GUS) gene, green fluorescent protein (GFP) gene, β-lactamase gene and chloramphenicol acetyltransferase (CAT) gene.

Techniques for plant transformation have already been established, among which the *Agrobacterium* method can be employed. This method is well known and can be used to transform both dicotyledonous and monocotyledonous plants (WO94/00977, WO95/06722). Gene introduction may also be accomplished, e.g., by electroporation which is a standard technique for protoplasts or by using a particle gun in a general manner. When used herein for genes, the term "introduce" or "introductions" means that a gene is put into a target plant (usually, plant cells) from outside, unless otherwise specified. The introduced gene is preferably integrated into the genome of the target plant.

Transformed cells may be selected by screening using an appropriate marker as an indicator. Transformed cells may be differentiated into transgenic plants of interest using conventional techniques.

Analysis of transformants may be carried out according to various procedures well known to those skilled in the art. For example, oligonucleotide primers are synthesized based on the DNA sequence of the introduced gene and then used in PCR to analyze the chromosomal DNAs of the transgenic plants. Alternatively, the analysis may also be accomplished by determining the presence or absence of mRNA or protein expression corresponding to the introduced gene. Further, the analysis may be accomplished by testing the resulting plants for their characteristics including cold tolerance. In a case where a genomic gene for PPDK is introduced, transformants may be analyzed for the expression level of PPDK. To determine whether transformants are cold-tolerant or not, the transformants themselves or PPDK collected therefrom may be analyzed for a decrease in PPDK activity when treated at low temperature. Procedures for these analyses are well known to those skilled in the art.

The transgenic plant of the present invention allows more expression of an enzyme constituting a photosynthetic pathway, when compared with a non-transgenic plant. The expression level is preferably an effective amount to enhance photosynthesis rate in the transgenic plant. The "effective amount to enhance photosynthesis rate" means that at a certain temperature, preferably at low temperature (e.g., at around 12° C., at around 0° C.), the transgenic plant allows more expression of the enzyme constituting a photosynthetic pathway when compared with a non-transgenic plant, so that the transgenic plant has a greater photosynthesis rate and/or it grows better or produces a desired product in a higher yield.

Further, in the transgenic plant of the present invention created using a modified genomic gene, an enzyme constituting a photosynthetic pathway is more highly expressed and/or is more resistant to deactivation, when compared with a non-transgenic plant. In this case, the level of expression/deactivation is preferably an effective amount/level to enhance photosynthesis rate in the transgenic plant. The "effective amount to enhance photosynthesis rate" is as stated previously. The "effective level to enhance photosynthesis rate" used for deactivation means that at a certain temperature, preferably at low temperature (e.g., at around 12° C., at around 0° C.), the enzyme in the transgenic plant is more resistant to deactivation when compared with a non-transgenic plant, so that the transgenic plant has a greater photosynthesis rate and/or it grows better or produces a desired product in a higher yield.

In addition to maize shown below in the Examples, the present invention can also be applied to other C4 plants including sugarcane, green amaranth, Japanese millet, foxtail millet, sorgum, millet and proso millet.

As used herein, the term "transgenic plant" encompasses not only transgenic plants ($T_0$ generation) regenerated from recombinant plant cells created according to the method of the present invention, but also progeny plants (e.g., $T_1$ generation) obtained from such transgenic plants as long as the progeny plants retain the introduced characteristics. Also, the term "plant" as used herein encompasses plant individuals as well as seeds (including germinated seeds, immature seeds), organs or portions thereof (including leaves, roots, stems, flowers, stamens, pistils, pieces thereof), cultured plant cells, calluses and protoplasts, unless otherwise specified.

The method of the present invention achieves more expression of an enzyme constituting a photosynthetic pathway (e.g., PPDK as an important enzyme in the C4 cycle, or a modified form thereof) in C4 plants. The method of the present invention further achieves enhancement of photosynthesis rate in C4 plants, enabling the C4 plants to attain cold tolerance. This in turn achieves increased production of C4 plants having PPDK, particularly increased production of maize or the like under low temperature conditions.

To date, there were some examples where a C4 plant genomic gene was expressed in C3 plants, but there was no case where a C4 plant genomic gene was introduced into C4 plants to achieve high-level expression of the gene. Since C3 plants are essentially free from genes involved in the C4 photosynthesis (or, if any, in very low amounts), C3 plants readily show effects of the introduced gene. According to the present invention, high-level expression of a C4 plant genomic gene can be achieved in C4 plants and effects of the introduced gene can be obtained without being masked by the corresponding endogenous gene. Also, in another embodiment of the present invention, the nature of a gene may be modified using point mutagenesis procedures to give greater effects under specific conditions (e.g., low temperature conditions), unlike simply improving the expression level. The present invention enables the PPDK gene involved in the C4 photosynthesis to be expressed in C4 plants at high level, thus achieving for the first time enhancement of photosynthesis rate in C4 plants, which has not been realized.

Although, as stated above, the method of the present invention is useful for transformation of an enzyme constituting the C4 photosynthetic pathway, the same procedures may also be adapted to provide C4 plants with other desired characteristics. Namely, the present invention also provides a method for highly expressing an object protein in a plant using an expression cassette that comprises a promoter, a plant genomic gene, under control of said promoter, encoding the object protein, and a terminator. The genomic gene as used here will preferably comprise a nucleotide sequence derived from the nucleotide sequence of the plant genome-derived gene encoding the object protein, by deletion, substitution, addition or insertion of one or more nucleotides in the exon(s) of the gene, with the introns of the gene retained. Although the method of the present invention is useful for transformation of C4 plants, the same procedures may also be adapted to transformation of other plants.

EXAMPLES

Example 1

(Construction of #2706)

In order to introduce the unmodified maize PPDK genomic gene into maize, a gene used for transformation (#2706) was constructed as follows.

A 4.5 kb BamHI fragment covering from the latter half of Intron 1 to the first half of Intron 6 was cleaved from the maize PPDK genome cloned in λongC (Matsuoka M, 1990) and then inserted into a BamHI site of pSB11 (Komari T, Hiei Y, Saito Y, Murai N, Kumashiro T, Vectors carrying two separate T-DNAs for co-transformation of higher plants mediated by Agrobacterium tumefaciens and segregation of transformants free from selection marker, Plant J, 10:165-175, 1996). This plasmid was digested with XbaI to remove the λ arm segment and then blunt-ended with Klenow enzyme. The resulting fragment was ligated to a similarly blunt-ended 2 kb EcoRI fragment (covering from the promoter region to the middle of Intron 1) cleaved from the PPDK genome cloned in λEMBL3 (Matsuoka M, 1990). Subsequently, a 3.3 kb BamHI fragment covering from the latter half of Intron 6 to the transcription termination region was cleaved from the λongC clone and then inserted into a BamHI site of the vector prepared above, covering from the promoter to the first half of Intron 6. Finally, the bar gene ligated to the maize ubiquitin promoter, maize introns and the nos terminator was inserted into a KpnI site (FIG. 1). The DNA sequence (promoter to terminator) of the finally constructed clone #2706 is shown in SEQ ID NO: 15.

(Creation and Evaluation of Transgenic Plants)

According to the Agrobacterium method, the gene for transformation (#2706) was introduced into a maize inbred line (A188) to create a transgenic plant. At that time, a gene resistant to the herbicide Basta was used as a selective marker. The resulting transgenic plant was inbred to produce its progeny of the next generation, which were then cultivated. Cut leaves were sampled at the young-seedling stage and put into a Basta-containing medium to classify the progeny plants between individuals homozygous or heterozygous for the introduced PPDK gene (homo or hetero) and individuals null for the gene (null) (Ming-Bo Wang, Peter M. Waterhouse, A rapid and simple method of assaying plants transformed with hygromycin or PPT resistance, Plant Molecular Biology Reporter, 15:209-215 (1997)).

Subsequently, a green leaf extract was collected from leaves of each plant and subjected to Western analysis to estimate the amount of PPDK present in each progeny plant.

Further, from knee-height stage to de-tasselling stage, the photosynthesis rate was determined using photosynthesis-measuring devices (Model LI-6400, LI-COR). Two devices were always used for determination to perform simultaneous measurement on a pair of the same transformant-derived homo or hetero individual and null individual (25 pairs). Conditions under the photosynthesis rate was determined were set as follows: light level in a chamber: constant at 1000 $\mu mol \cdot m^{-2} \cdot s^{-1}$ (LED source of artificial light); $CO_2$ level in a chamber: constant at 350 $\mu mol \cdot CO_2 mol^{-1}$; humidity in a chamber: not controlled in principle (loosely controlled within a range where measurement was not affected); and air stream (flow rate) in a chamber: constant at 500 μmol·s⁻¹. The photosynthesis rate was determined at leaf surface temperatures of 30° C., 20° C., 13° C. and 8° C. For determination under low temperature conditions, the photosynthesis-measuring devices and plants (leaves only) were transferred into a refrigerating room where the determination was performed. Data analysis was made by paired t-test.

(Results)

Figure 2A:
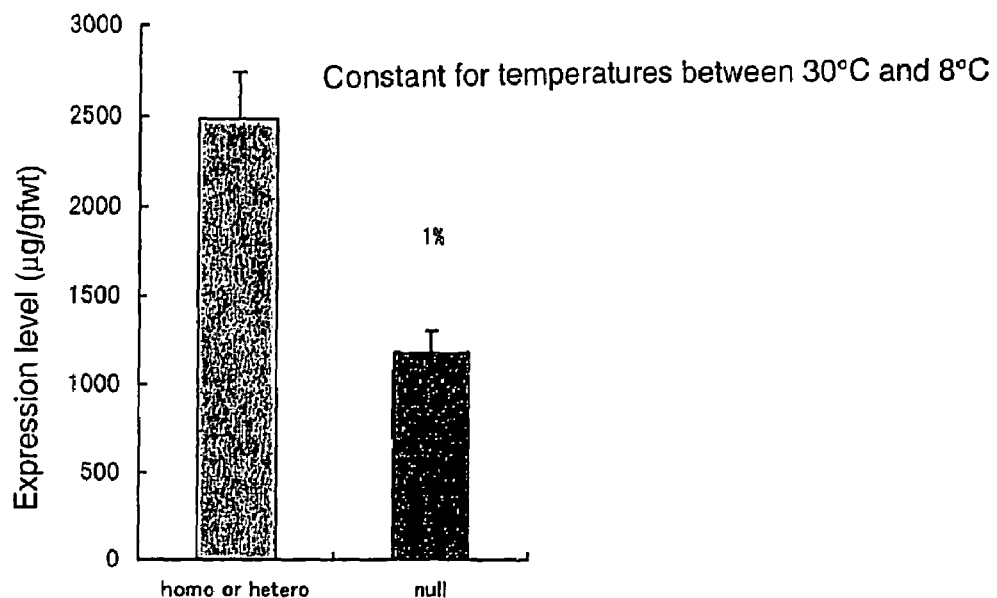
FIG. 2A shows the amount of PPDK present in progeny plants of transformants modified with a maize genomic gene (#2706), compared between individuals homozygous or heterozygous for the introduced PPDK gene (homo or hetero) and individuals null for the gene (null). The vertical axis represents the expression level (μg/gfwt) of PPDK contained per g of fresh green leaves, and each bar represents standard error. There was a significant difference between homo or hetero individuals and null individuals at a significance level of 1%.

The amount of PPDK contained per g of fresh green leaves is, on average, 2484.0 μg/gfwt in the homo or hetero group and 1179.6 μg/gfwt in the null group. There was a significant difference between them at a significance level of 1%, as analyzed by paired t-test. This indicated that the introduction of the maize PPDK genomic gene resulted in an increase in the expression level of PPDK (FIG. 2A).

Figure 2B:
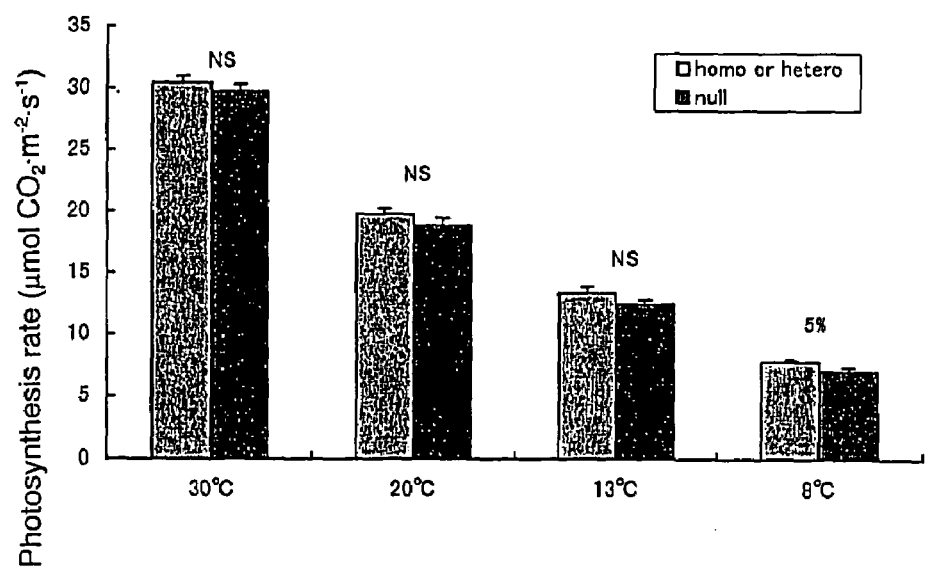
FIG. 2B shows the photosynthesis rate at various leaf surface temperatures in progeny plants of transformants modified with a maize genomic gene (#2706), compared between homo or hetero individuals and null individuals. The vertical axis represents the photosynthesis rate ($\mu mol\ CO_2 \cdot m^{-2} \cdot s^{-1}$), and each bar represents standard error. At a leaf surface temperature of 8° C., there was a significant difference between homo or hetero individuals and null individuals at a significance level of 5%.

This increase in the expression level of PPDK was also as much as sufficient to clarify effects of the introduced gene. At a leaf surface temperature of 8° C., the photosynthesis rate was found to be improved in the homo or hetero individuals when compared with null individuals (at a significance level of 5%) (FIG. 2B).

Example 2

Next, the inventors of the present invention attempted to modify the maize PPDK genomic gene into a cold-tolerant type. In the previous studies, the inventors of the present invention had already succeeded in artificially creating a cold-tolerant PPDK gene by forming a chimeric gene between cDNAs (WO95/15385). They in turn created a modified maize PPDK genomic gene whose sequence was partially replaced with the *F. brownii* PPDK cDNA such that the resulting spliced mRNA was identical with mRNA prepared from the cold-tolerant chimeric gene between cDNAs. This chimeric gene was then introduced into maize, but resulting in low level expression. This result would be brought about by elimination of introns naturally occurring in the genomic gene due to partial replacement of the genomic gene with the cDNA.

For this reason, with the aim of modifying the maize PPDK genomic gene into a cold-tolerant type while leaving its structure as intact as possible, point mutations were introduced to construct a cold-tolerant modified maize PPDK genomic gene (#2838) as follows.

(Construction of #2838)

Figure 3:
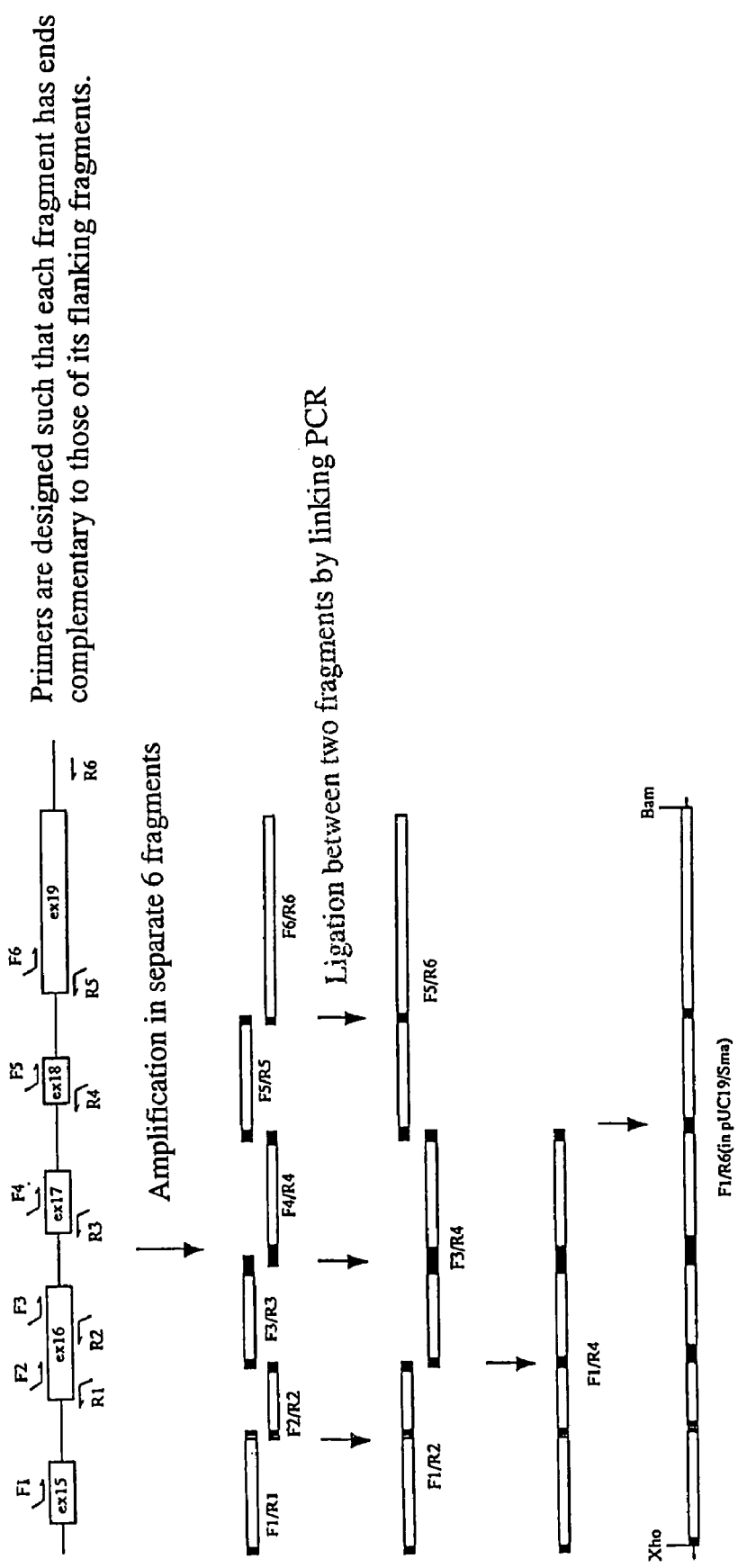
FIG. 3 shows procedures for introduction of F. brownii-type mutations into the PPDK genome.

Introduction of these mutations into the genomic clone was carried out by PCR (Ho S N, Hunt H D, Horton R M, Pullen J K, Pease L R, Site-directed mutagenesis by overlap extension using the polymerase chain reaction, Gene 77:51-59 (1989)). As a PCR polymerase, ExTaq or Pyrobest (both available from Takara Shuzo Co., Ltd.) was used in order to minimize amplification errors and each fragment was subcloned every step into the plasmid vector pCR2.1 or pUC19 to confirm that there was no error in its nucleotide sequence. The mutations were introduced such that the amino acid sequence was equivalent to *F. brownii* PPDK, and codons used for this purpose were selected from those which occurred frequently in the maize PPDK gene. First, an approximately ⅙ region from the C-terminal of PPDK, which was important for cold tolerance (Ohta S et al., (1996); corresponding to Exon 15 and its downstream region) was divided into 6 fragments and these separate fragments were amplified using primer sets carrying mutations: F1 & R1, F2 & R2, F3 & R3, F4 & R4, F5 & R5 and F6 & R6 (SEQ ID NOs: 1 to 6 and 8 to 13). Flanking two fragments were successively ligated together by PCR and Fragments 1 to 4 were then ligated into one fragment. Finally, all fragments were ligated together to complete a XhoI-BamHI fragment (FIG. 3).

Figure 4:
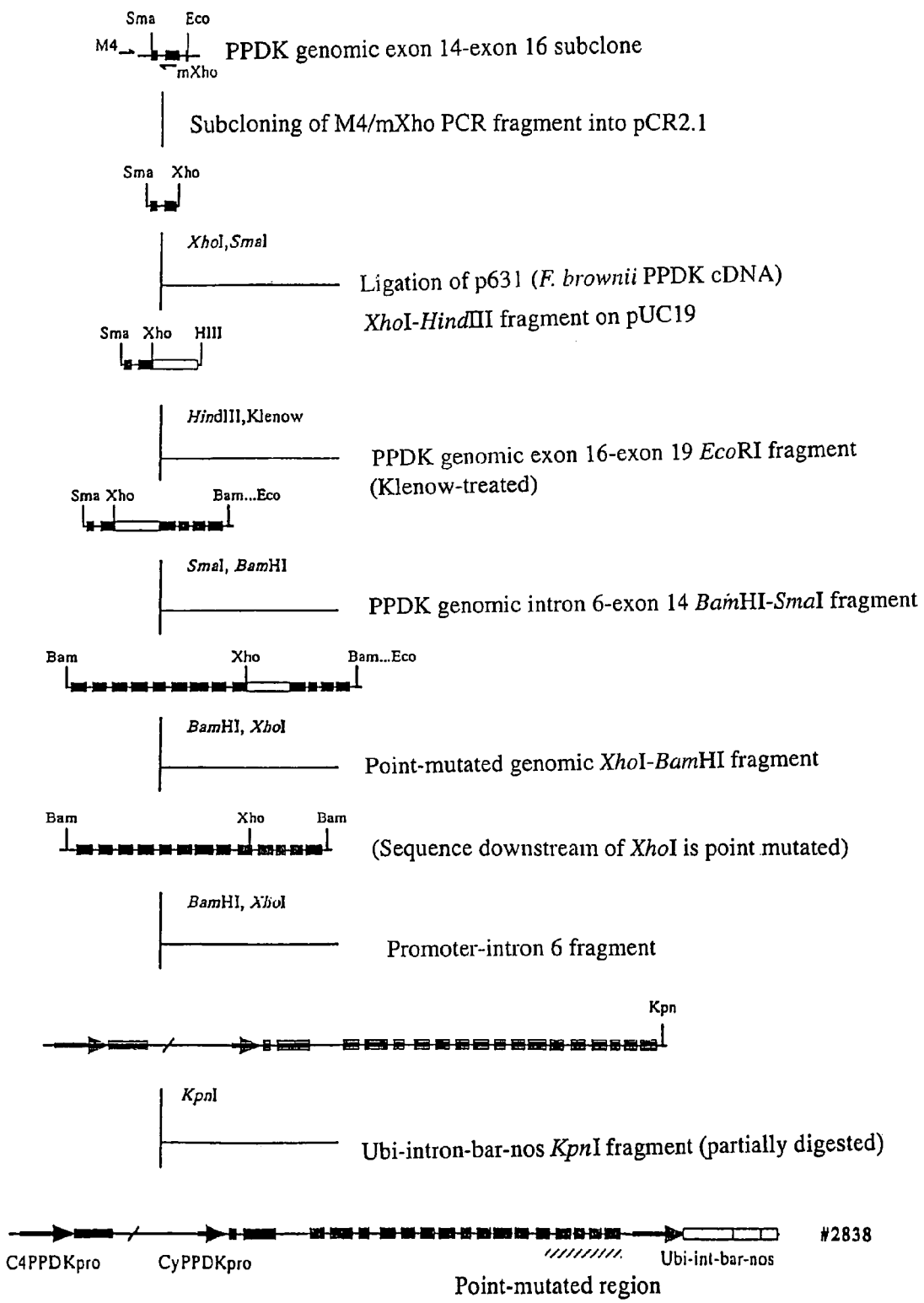
FIG. 4 shows procedures for construction of #2838 in Example 2.

Meanwhile, a SmaI-EcoRI fragment covering from the latter half of Exon 14 to the first half of Exon 16 of the maize PPDK genomic clone was subsloned into pUC18, followed by introduction of a XboI site into Exon 15 by PCR using the primer set M4 (SEQ ID NO: 7) and mXho (SEQ ID NO: 14). This fragment was ligated to the XboI-BamHI fragment prepared above to replace the corresponding region in the 3.3 kb BamHI fragment. This fragment was inserted into a BamHI site of the vector covering from the promoter to the first half of Intron 6. Finally, the bar gene ligated to the maize ubiquitin promoter, maize introns and the nos terminator was inserted into a KpnI site (FIG. 4). The DNA sequence (promoter to terminator) of the finally constructed clone #2838 is shown in SEQ ID NO: 16.

The amino acid sequence covering an approximately ⅙ region from the C-terminal of *F. brownii* PPDK, which is important for cold tolerance (said amino acid sequence corresponding to the sequence downstream of No. 7682 in SEQ ID NO: 16) is shown in FIG. 5 along with the amino acid sequence covering the same region of the maize PPDK gene (said amino acid sequence corresponding to the sequence downstream of No. 7682 in SEQ ID NO: 15).

(Creation and Evaluation of Transgenic Plants)

In the same manner as shown in Example 1, the point-mutated cold-tolerant maize PPDK genomic gene (#2838) was introduced into a maize inbred line (A188) to create a transgenic plant.

Subsequently, in the same manner as shown in Example 1, the progeny plants were classified between homo or hetero individuals and null individuals, followed by Western analysis to estimate the amount of PPDK and determination of the photosynthesis rate. As in Example 1, two devices were always used for determination of the photosynthesis rate to perform simultaneous measurement on a pair of the same transformant-derived homo or hetero individual and null individual. Data analysis was also made by paired t-test.

(Result 1)

Figure 6A:
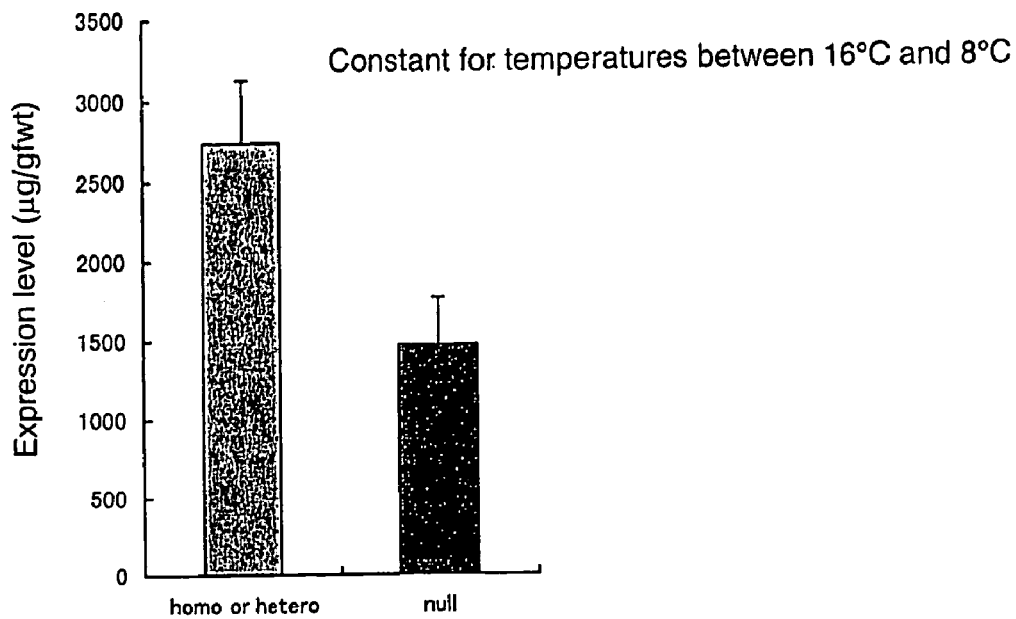
FIG. 6A shows the amount of PPDK present in progeny plants of transformants modified with a mutated maize genomic gene (#2838), compared between homo or hetero individuals and null individuals. The vertical axis represents the expression level (μg/gfwt) of PPDK contained per g of fresh green leaves, and each bar represents standard error.

The amount of PPDK is, on average, 2742.2 μg/gfwt in the homo or hetero group and 1471.8 μg/gfwt in the null group (FIG. 6A). This indicated that the introduction of the point-mutated cold-tolerant maize PPDK genomic gene resulted in an increase in the expression level of PPDK.

Figure 6B:
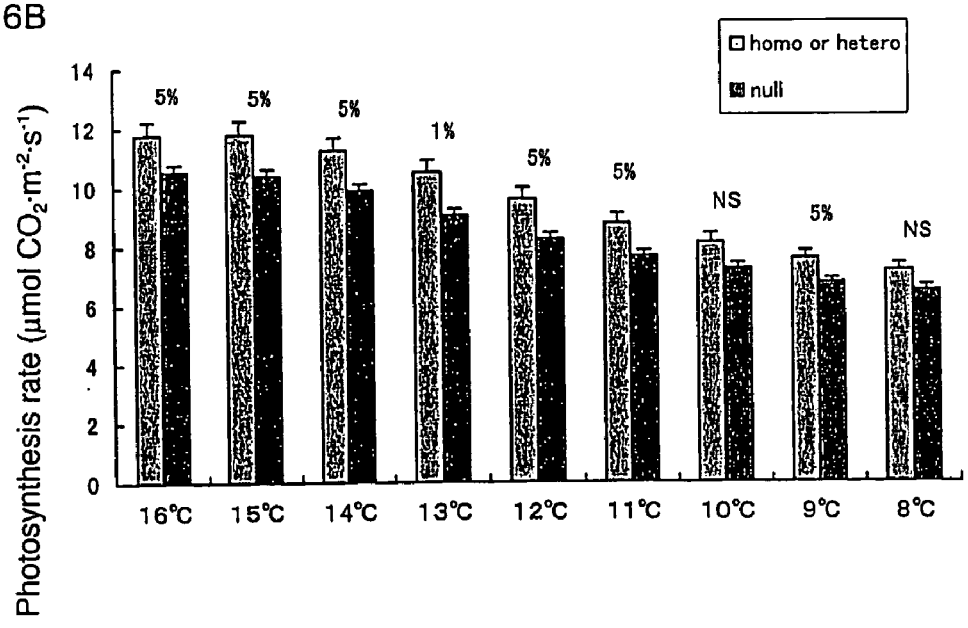
FIG. 6B shows the photosynthesis rate at various leaf surface temperatures in progeny plants of transformants modified with #2838, compared between homo or hetero individuals and null individuals. The vertical axis represents the photosynthesis rate ($\mu mol\ CO_2 \cdot m^{-2} \cdot s^{-1}$), and each bar represents standard error.

Also, the photosynthesis rate was found to be improved in the homo or hetero individuals when compared with null individuals (analysis on 15 pairs) (FIG. 6B).

(Result 2)

Figure 7A:
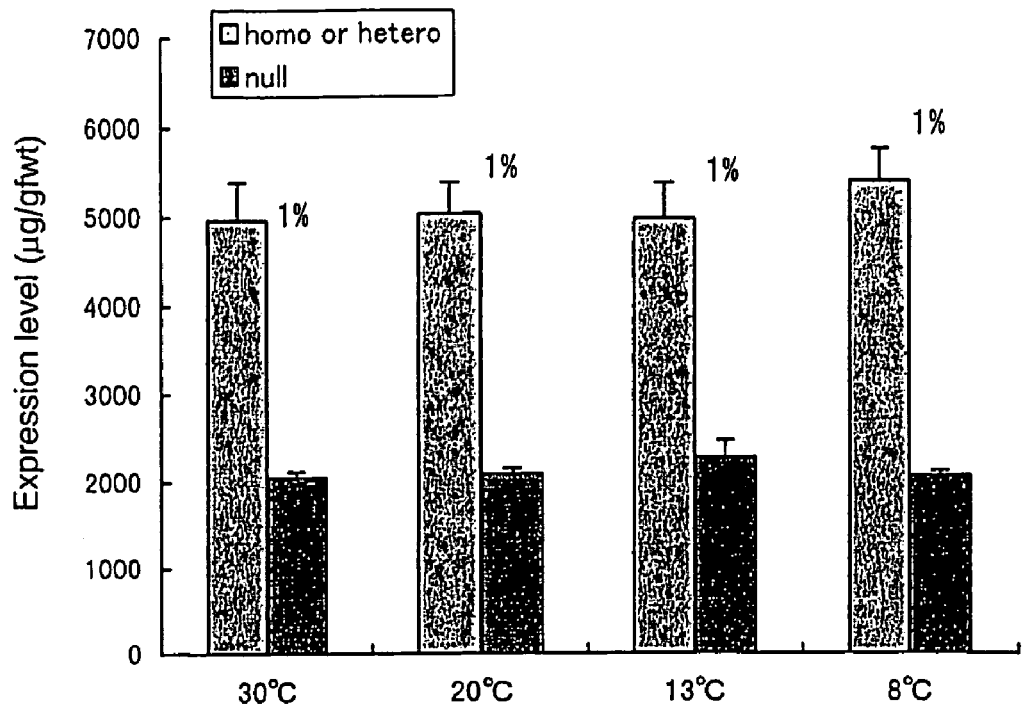
FIG. 7A shows the amount of PPDK present at various leaf surface temperatures in progeny plants of transformants modified with a mutated maize genomic gene (#2838), compared between homo or hetero individuals and null individuals. The vertical axis represents the expression level (μg/gfwt) of PPDK contained per g of fresh green leaves, and each bar represents standard error.

The number of plants used for determination of the photosynthesis rate was 15 pairs at 30° C., 19 pairs at 20° C. and 21 pairs at 8° C. The amount of PPDK is shown for the respective temperatures (FIG. 7A). The homo or hetero individuals far exceeded the null individuals (at a significance level of 1%).

Figure 7B:
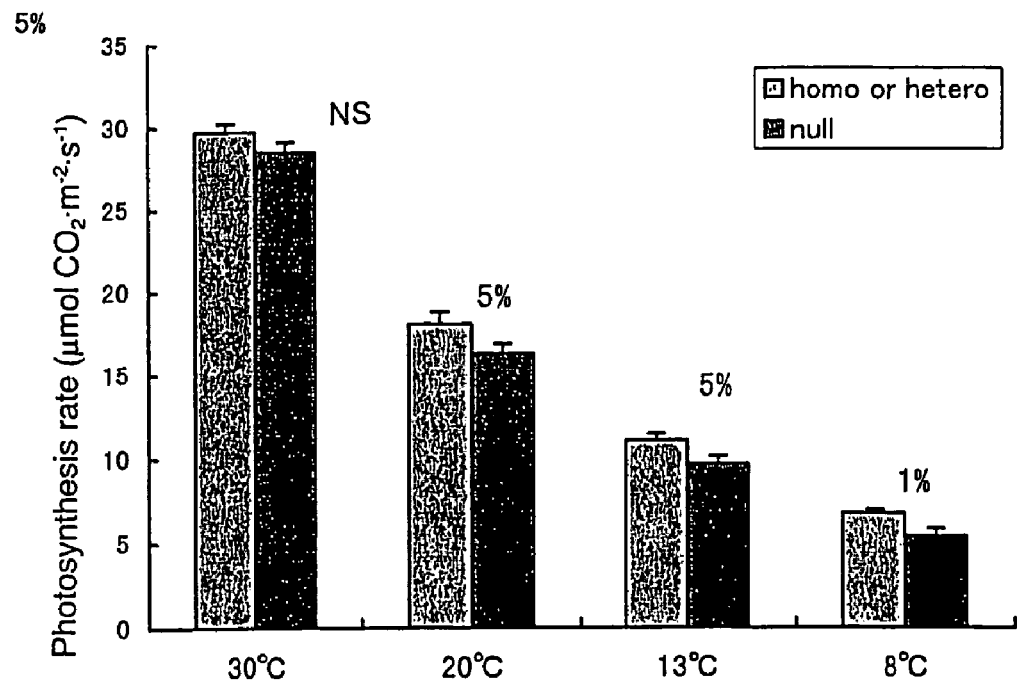
FIG. 7B shows the photosynthesis rate at various leaf surface temperatures in progeny plants of transformants modified with #2838, compared between homo or hetero individuals and null individuals. The vertical axis represents the photosynthesis rate ($\mu mol\ CO_2 \cdot m^{-2} \cdot s^{-1}$), and each bar represents standard error. At leaf surface temperatures of 20° C. and 13° C., there was a significant difference between homo or hetero individuals and null individuals at a significance level of 5%. At a leaf surface temperature of 8° C., there was a significant difference at a significance level of 1%.

Also, the photosynthesis rate was found to be improved in the homo or hetero individuals when compared with null individuals (FIG. 7B).

These results indicated that the introduction of the point-mutated cold-tolerant maize PPDK genomic gene resulted in an extremely large increase in the expression level of PPDK and a further improvement in photosynthesis rate, as compared with simple introduction of the unmodified genomic PPDK. Namely, the inventors of the present invention found that the photosynthesis rate was improved even in a temperature range where no difference was observed by simply improving the expression level.

Example 3

Further, the inventors of the present invention examined PPDK activity in the transgenic maize plants having the cold tolerance-improved genomic gene introduced thereinto. In the experiment, several maize plants with different expression levels of PPDK were used along with *F. brownii* and a maize inbred line (A188) as controls. A green leaf extract collected from leaves of each plant was desalted on a Sephadex G25 column and then allowed to stand at 0° C. (on ice), followed by periodical verification of PPDK activity to monitor the time course of the change in PPDK activity under low temperature conditions. PPDK activity was determined in a general manner (Jenkins C L, Hatch M D, Properties and reaction mechanism of C4 leaf pyruvate, Pi dikinase, Arch Biochem Biophys, 239:53-62, 1985).

Figure 8:
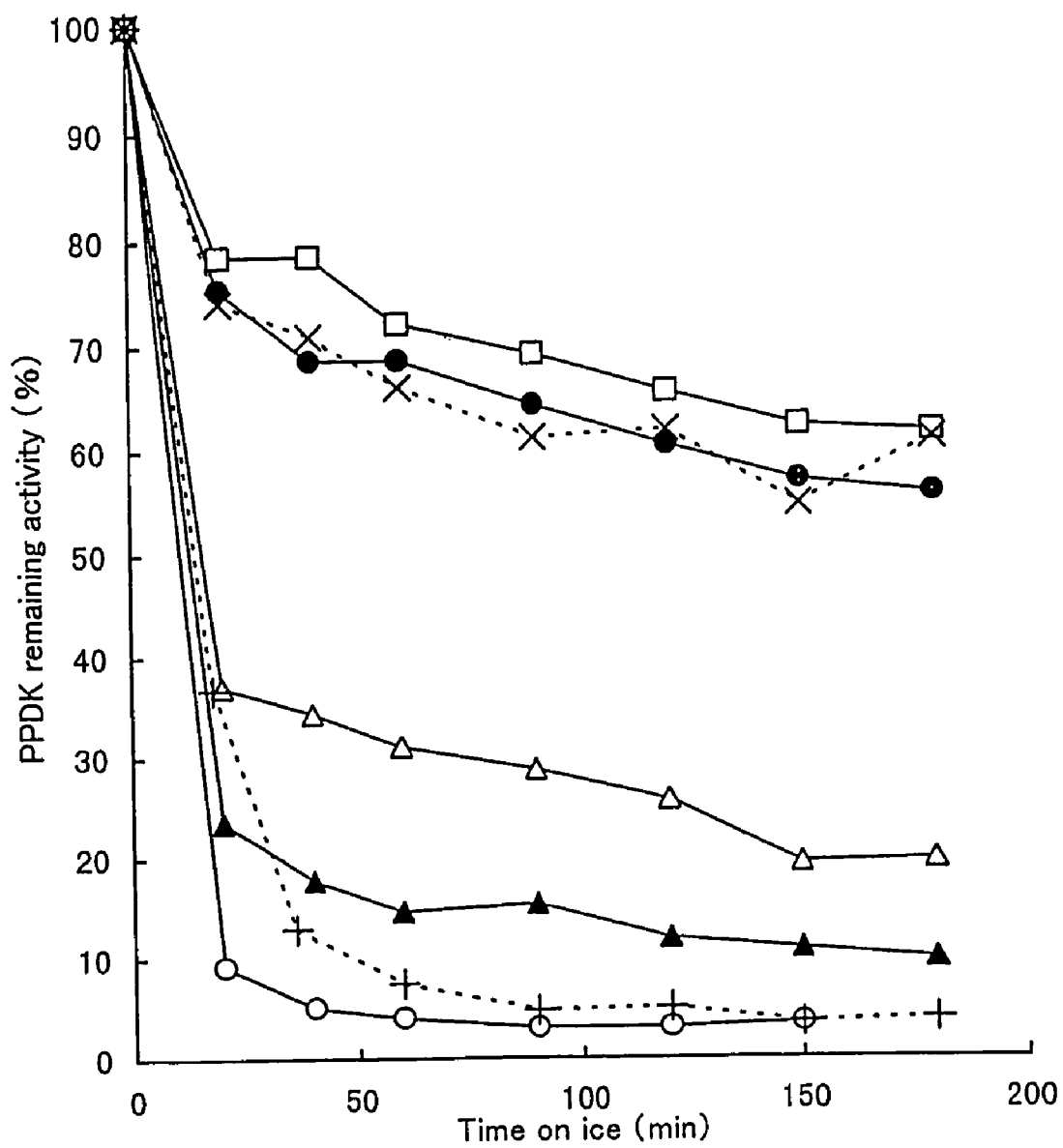
FIG. 8 shows a cold inactivation pattern of PPDK in transformants with a mutated maize genomic gene. The horizontal axis represents time on ice (min), while the vertical axis represents PPDK activity (%). Open triangle (Δ), open square (□), solid triangle (▲), solid circle (●) and open circle (○) represents transformants with PPDK contents of 4152.3 μg/gfwt, 9122.4 μg/gfwt, 1390.6 μg/gfwt, 9802.8 μg/gfwt and 1292.1 μg/gfwt, respectively, relative to 1 g of desalted fresh green leaves. Cross (×) represents *F. brownii* and plus (+) represents the maize inbred line A188 (1495.2 μg/gfwt). Transformants with high PPDK contents could retain their PPDK activity, even on ice, at almost the same level as *F. brownii*.

The results are shown in FIG. 8. It could be confirmed that transformants with high expression levels of PPDK were resistant to deactivation, even on ice, as in the case of *F. brownii*.

The invention claimed is:

1. A method for increasing the expression level of pyruvate orthophosphate dikinase (PPDK) in a C4 plant, comprising the steps of:
   (i) transforming the C4 plant using an expression cassette that comprises: a promoter; an isolated DNA from a 04 plant genome encoding PPDK, operably linked to said promoter; and a terminator; wherein said DNA comprises a nucleotide sequence having at least 98% sequence identity to the nucleotide sequence as set forth in nucleotides 1732-8508 of SEQ ID NO:15 and encodes a protein having PPDK activity; and
   (ii) expressing said DNA in said C4 plant, wherein expression of said PPDK is increased in the C4 plant.

2. The method according to claim 1, wherein said DNA consists of the nucleotide sequence as set forth in nucleotides 1732-8508 of SEQ ID NO:15.

3. The method according to claim 1, wherein said C4 plant is maize.

4. The method according to claim 1, wherein said DNA comprises a sequence having nucleotides 1732-8508 of SEQ ID NO:15.

* * * * *

SEQUENCE LISTING

<160> NUMBER OF SEQ ID NOS: 19

<210> SEQ ID NO 1
<211> LENGTH: 27
<212> TYPE: DNA
<213> ORGANISM: Artificial Sequence
<220> FEATURE:
<223> OTHER INFORMATION: Synthetic PCR forward primer (F1)

<400> SEQUENCE: 1
ctcgagcagc tctgatcgct gatgagg                                     27

<210> SEQ ID NO 2
<211> LENGTH: 20
<212> TYPE: DNA
<213> ORGANISM: Artificial Sequence
<220> FEATURE:
<223> OTHER INFORMATION: Synthetic PCR forward primer (F2)

<400> SEQUENCE: 2
gatagcgaag gaggctgaat                                             20

<210> SEQ ID NO 3
<211> LENGTH: 25
<212> TYPE: DNA
<213> ORGANISM: Artificial Sequence
<220> FEATURE:
<223> OTHER INFORMATION: Synthetic PCR forward primer (F3)

<400> SEQUENCE: 3
cccatctatc tttcccaggg cattc                                       25

<210> SEQ ID NO 4
<211> LENGTH: 44
<212> TYPE: DNA
<213> ORGANISM: Artificial Sequence
<220> FEATURE:
<223> OTHER INFORMATION: Synthetic PCR forward primer (F4)

<400> SEQUENCE: 4
tcaagatggc tacagagaag ggccgcgccg ctaaccctaa cttg                  44

<210> SEQ ID NO 5
<211> LENGTH: 21
<212> TYPE: DNA
<213> ORGANISM: Artificial Sequence
<220> FEATURE:
<223> OTHER INFORMATION: Synthetic PCR forward primer (F5)

<400> SEQUENCE: 5
ttcgacgggg ttgggctgga t                                           21

-continued

```
<210> SEQ ID NO 6
<211> LENGTH: 17
<212> TYPE: DNA
<213> ORGANISM: Artificial Sequence
<220> FEATURE:
<223> OTHER INFORMATION: Synthetic PCR forward primer (F6)

<400> SEQUENCE: 6
ctcaggtggt tgtctga                                                    17

<210> SEQ ID NO 7
<211> LENGTH: 17
<212> TYPE: DNA
<213> ORGANISM: Artificial Sequence
<220> FEATURE:
<223> OTHER INFORMATION: Synthetic PCR forward primer (M4)

<400> SEQUENCE: 7
gttttcccag tcacgac                                                    17

<210> SEQ ID NO 8
<211> LENGTH: 17
<212> TYPE: DNA
<213> ORGANISM: Artificial Sequence
<220> FEATURE:
<223> OTHER INFORMATION: Synthetic PCR reverse primer (R1)

<400> SEQUENCE: 8
cctccttcgc tatctgc                                                    17

<210> SEQ ID NO 9
<211> LENGTH: 25
<212> TYPE: DNA
<213> ORGANISM: Artificial Sequence
<220> FEATURE:
<223> OTHER INFORMATION: Synthetic PCR reverse primer (R2)

<400> SEQUENCE: 9
aagatagatg ggaaggaact ttccc                                           25

<210> SEQ ID NO 10
<211> LENGTH: 43
<212> TYPE: DNA
<213> ORGANISM: Artificial Sequence
<220> FEATURE:
<223> OTHER INFORMATION: Synthetic PCR reverse primer (R3)

<400> SEQUENCE: 10
ctctgtagcc atcttgatca gctggcccac tcccttctgg tcc                       43

<210> SEQ ID NO 11
<211> LENGTH: 21
<212> TYPE: DNA
<213> ORGANISM: Artificial Sequence
<220> FEATURE:
<223> OTHER INFORMATION: Synthetic PCR reverse primer (R4)

<400> SEQUENCE: 11
cccaaccccg tcgaagaagg c                                               21

<210> SEQ ID NO 12
<211> LENGTH: 17
<212> TYPE: DNA
<213> ORGANISM: Artificial Sequence
<220> FEATURE:
```

```
<223> OTHER INFORMATION: Synthetic PCR reverse primer (R5)

<400> SEQUENCE: 12
tcagacaacc acctgag                                                  17

<210> SEQ ID NO 13
<211> LENGTH: 17
<212> TYPE: DNA
<213> ORGANISM: Artificial Sequence
<220> FEATURE:
<223> OTHER INFORMATION: Synthetic PCR reverse primer (R6)

<400> SEQUENCE: 13
ggatcctagc gacatgc                                                  17

<210> SEQ ID NO 14
<211> LENGTH: 21
<212> TYPE: DNA
<213> ORGANISM: Artificial Sequence
<220> FEATURE:
<223> OTHER INFORMATION: Synthetic PCR reverse primer (mXho)

<400> SEQUENCE: 14
ctcgagggat ctcaatcatt g                                             21

<210> SEQ ID NO 15
<211> LENGTH: 8820
<212> TYPE: DNA
<213> ORGANISM: maize
<220> FEATURE:
<223> OTHER INFORMATION: DNA sequence of clone #2706 (promoter to
      terminator). Maize genomic DNA.

<400> SEQUENCE: 15
gaattcccat tttttgttgt tgtcaaaat aatcattgtt tggtcagtgg ttgttaggaa      60
ggaggtggat agaaagttaa atttagattt tccctggggt ggaggacatg aaagagtggg    120
aaaggttgct ggacattttg aaggagtga taattactaa acgagaatat atgttatctt     180
cgtcgttaga gaaatctaga cagtatacaa caagatccac gtactatagg taaacttttta  240 ggggtattgt gaacaagagg atgagtaaac tctaaaagaa caaagctcca atgaaaattt    300
aggtttttat gtggtagtc atagggcaag ttgcaaacag gtgttgatct aaaaggaag     360 tagtagggaa atgtgaagtg tctttgcgag gaattggaaa atgaagatca catttttcttt  420 gggtgcatca tggaagaac catttgggac tcttttaagg aggcctaaga atgccataaa    480
gtttgcaaga tcttttgaa gagtgtctac ctataaacaa tagtaaatat catgtcaaat    540
ttttcatctt cgccattatt ctttaggaga atttagaatg ttccgaataa aatatggata   600
gaaaagaagt tcccaaagtc atccaatttt ctacaaaatc ttcaacttta agattgagag   660
tgagtgttgt aaagttcttg gaagatgagt tgaaccccat ggaggcgttg gctaaagtac   720
tgaaagcaat ctaaagacat ggaggtggaa ggcctgacgt agatagagaa gatgctctta   780
gctttcattg tctttctttt gtagtcatct gatttacctc tctcgtttat acaactggtt   840
ttttaaacac tccttaactt ttcaaattgt ctctttcttt accctagact agataatttt   900
aatggtgatt ttgctaatgt ggcgccatgt tagatagagg taaatgaac tagttaaaag    960 ctcagagtga taaatcaggc tctcaaaaat tcataaactg ttttttaaat atccaaatat  1020
ttttacatgg aaaataataa aatttagttt agtattaaaa attcagttga atatagtttt  1080
gtcttcaaaa attatgaaac tgatcttaat tattttcct taaaaccgtg ctctatcttt  1140
```

```
gatgtctagt tgagacgat tgtataattt ttttgtgctt atctacgacg agctgaagta    1200
cgtagaaata ctagtggagt cgtgccgcgt gtgcctgtag ccactcgtac gctacagccc    1260
aagcgctaga gcccaagagg ccggaggtgg aaggcgtcgc ggcactatag ccactcgccg    1320
caagagccca agaggccgga gctggaagga tgagggtctg ggtgttcacg aattgcctgg    1380
aggcaggagg ctcgtcgtcc ggagccacag gcgtggagac gtccgggata aggtgagcag    1440
ccgctgcgat aggggcgcgt gtgaacccccg tcgcgcccca cggatggtat aagaataaag    1500
gcattccgcg tgcaggattc acccgttcgc ctctcacctt ttcgctgtac tcactcgcca    1560
cacacacccc ctctccagct ccgttggagc tccggacagc agcaggcgcg gggcggtcac    1620
gtagtaagca gctctcggct ccctctcccc ttgctccata tgatcgtgca acccatcgag    1680
ctacgcgcgt ggactgcctt ccctgggtcg gcgcaggagg ggatcggaag gatgacggca    1740
tcggtttcca gggccatctg cgtacagaag ccgggctcaa aatgcaccag ggacagggaa    1800
gcgacctcct tcgcccgccg atcggtcgca gcgccgaggc ccccgcacgc caaagccgcc    1860
ggcgtcatcc gctccgactc cggcgcggga cggggccagc attgctcgcc gctgagggcc    1920
gtcgttgacg ccgcgccgat acagacgacc aaaaaggtat cccttgcagc tcttagaaac    1980
tgaattctag aggttcaggg ttgtatatcc acaatctagt ttatccacca ttaataagat    2040
ataatttgtt acgcgtggc aatgcacttc cacgaactcc tgaggcagcg gataatgttt    2100
aaaaacgcat ttttgtcaac caggattaag aagctcattt tgagtttgcc cccatttggt    2160
tagaacatgg aacacgttct gcatatagtt ttcctctggg taagattgcg tagcgatcag    2220
gttttcggat cttccactcc gttttcccgt cgtcatacgt aggcgtagcg gtccacctca    2280
ttcgttcact tgtagttgta gctaggaagc tctctcccaa cggcgtgccg cacactctt    2340 tgccggcccg acgcaaaaat ggcatgaatt tgctccaccg tgtttacata tgtaggagaa    2400
cttggataaa actgtgtaaa tactgcaaca catggatatg ggcactgtag tttaccctac    2460
cttaattaag caccaagctg cggcagagcg gctcggagtg cgtgcaaaaa cgacagccat    2520
ccgtgcgctc tccttgtggc ttctgcaggc tgcagcagct gccacccgcc cgcgccatgg    2580
acgcacggtg gacggtgctc tgcgcctctg cctatctccc gggaacgccg tgaccgggta    2640
ctagctagct tgaacgggat accaggcgga gacgccgcg gatttgcgga agcgtatcgc    2700
cggccgtgct gcgatctata tcccatcgtc taacaggcga cccatccagc tgacgcgacg    2760
aattaacaac gctatccgcg cgcatgcatg gccatgactt ggctattttg cactgtgcaa    2820
atgtctgccc agtagttcat ctcacgaaca caaatgccgg tggtcagtag gagagagaag    2880
aactaactcc agcgtccgat cgggacgcca ctcgctcgct cacaagcaaa gacactagct    2940
agtctcaact ctcaactaca acaacgctag taaagcctaa aacacacaca cgcacgcaca    3000
cacaagcaaa gcgagcaacg tacgttcgtc agtgcgtcct tgtgaaacag aaagcgcgcg    3060
ctctagctat agctgcaccg tgtctgcatg cgtgctgaca cgacagggtg agtcacacag    3120
aagcggcgct tggacgctag cagcacgatc agttcagttt ttcagcgttt ctttttttt    3180 ctggctggat atgcatcacg catggaacaa gagggtgtga catgcacgcc cagtggtggt    3240
cgttcttgca ttgcatttgg gctctgtatg atttaagatg gagggagtag cacaagtgta    3300
gttggcaggc tatttaccga tgatcaattt ttattaccag gtactctatc aaacaagtag    3360
tagctctact gttaaattag tctaacaagt gtagttggca cgtagggaag caagcccatg    3420
ttgatctgag gtgccgcgg gcgtccggaa ctccggatat gtatgctcgc tgctaccggc    3480
cagtaagctg gggcatgcgt gcgttcactt gcttgagacc gtttctaact ttgcaaacaa    3540
```

```
aaaaaaaaca accagcacca gactacgtga cgtgtaaagc tcatcctgac tgtttattgc    3600
tgcctgtttg tgaagaaaga aagaaaaaaa aaaagagaga gtcggccggg ctgctgcaca    3660
cgcacatcac tcgcggccgc cgctgctata aatagagccc ggggcaggcc ctgcttaatt    3720
catcaccagc cacggctgca tttatttgtc actgatcgtt gatcagccta gctagctagc    3780
gctgttttcc tgtgtgctaa tggcgcccgt tcaatgtgcg cgttcgcaga gggtgttcca    3840
cttcggcaag ggcaagagcg agggcaacaa gaccatgaag gaactggtga gaggtttctt    3900 cttttctgtat tctcgcttaa tctgcatgca tgcatgcata catactaatg aagtaataac    3960
gatgctgtcg atgaatgatg acgcatgcag ctgggcggca agggcgcgaa cctggcggag    4020
atggcgagca tcgggctgtc ggtgccgcca gggttcacgg tgtcgacgga ggcgtgccag    4080
cagtaccagg acgccgggtg cgccctcccc gcggggctct gggccgagat cgtcgacggc    4140
ctgcagtggg tggaggagta catgggcgcc accctgggcg atccgcagcg cccgctcctg    4200
ctctccgtcc gctccggcgc cgccgtgtcc atgcccggca tgatggacac ggtgctcaac    4260
ctggggctca cgacgaagt ggccgccggg ctggcggcca agagcgggga gcgcttcgcc    4320
tacgactcct tccgccgctt cctcgacatg ttcggcaacg tcgtgagtat cccccgcgcc    4380
gtagcatgcg tcttcgattc cgcgccctga ctcagctcct cgcttccatt cccgtccgcc    4440
ggttgttgtt actgctagct tgtcccacta gctaggtgca gtaggtgcct agttttgcgc    4500
gcatcgcgtc gcgtcgacga cgacccatcc tccaccgcgc tgccgtggcc gcaaccaagg    4560
ctggatggag cttttgtctg tttgccaggc cagccgttgc tttgggttaa aagtgcaaaa    4620
aaaaaatgat gaaggtcacg ctacgaacta aacagaccat atacgtacgg catcggcatg    4680
taaacttggc ttgtcggact cgagaaacga aagaacgatg actcaaactg ctctcagatt    4740
ttgtttcatt gtttgtgttt accaggtcat ggacatcccc cgctcactgt tcgaagagaa    4800
gcttgagcac atgaaggaat ccaagggggct gaagaacgac accgacctca cggcctctga    4860
cctcaaagag ctcgtgggtc agtacaagga ggtctacctc tcagccaagg gagagccatt    4920
cccctcaggt acataccggc ccgtcgatcg tcctcagctc tactgatcga tggagctagc    4980
ggtcagtttc cctgtgcacc gaaatcatgt gcttgcctgc cttgcagacc ccaagaagca    5040
gctggagcta gcagtgctgg ctgtgttcaa ctcgtgggag agccccaggg ccaagaagta    5100
caggagcatc aaccagatca ctggcctcag gggcaccgcc gtgaacgtgc agtgcatggt    5160
gttcggcaac atggggaaca cttctggcac cggcgtgctc ttcaccagga accccaacac    5220
cggagagaag aagctgtatg cgcagttcct ggtgaacgct caggtatgag tcggccctca    5280
ggcttccatt gcgcgcctgt tcgtgcatgg atacacgtac gtacgttact tgacgccatg    5340
catgcaattc gtttcctgct cagggtgagg atgtggttgc cggaataaga accccagagg    5400
accttgacgc catgaagaac ctcatgccac aggcctacga cgagcttgtt gagaactgca    5460
acatcctgga gagccactac aaggaaatgc aggtacagtt taattttcac cttctaattt    5520
aaacaccaca ccaccgtctc tctctctctc tctggatcct gatgtttctt ctccagatga    5580
tgtgagctca ggctgagact tggttttttct ttggcgtgtg tgatcatgca ggatatcgag    5640
ttcactgtcc aggaaaacag gctgtggatg ttgcagtgca ggacaggaa acgtacgggc    5700 aaaagtgccg tgaagatcgc cgtggacatg gttaacgagg gccttgttga gccccgctca    5760
gcgatcaaga tggtagagcc aggccacctg gaccagcttc tccatcctca ggtaatctat    5820
cgatcaagaa ccatggacgt acgtactaag ggcttaccaa atcaatcctt actaatgccg    5880
```

```
ttatgcattg atgccgttat ggaaacccac agtttgagaa cccgtcggcg tacaaggatc    5940
aagtcattgc cactggtctg ccagcctcac ctggggctgc tgtgggccag gttgtgttca    6000
ctgctgagga tgctgaagca tggcattccc aagggaaagc tgctattctg gtaatattca    6060
tcgcaaaaca ctttttattt ggactgcttt tccatacaac attttcacca gttttttgtaa   6120 atatatatac tgtatactgt atgcaggtaa gggcagagac cagccctgag gacgttggtg    6180
gcatgcacgc tgctgtgggg attcttacag agaggggtgg catgacttcc cacgctgctg    6240
tggtcgcacg tgggtggggg aaatgctgcg tctcgggatg ctcaggcatt cgcgtaaacg    6300
atgcggagaa ggtgacttga atcctctgt tacgcaagga agctccagca tgtctcgtga     6360
tttaccttgc tgtttattta tatgaattag ctcgtgacga tcggaggcca tgtgctgcgc    6420
gaaggtgagt ggctgtcgct gaatgggtcg actggtgagg tgatccttgg gaagcagccg    6480 cttccccac cagcccttag tggtgatctg ggaactttca tggcctgggt ggatgatgtt     6540
agaaagctca aggtaaaaat cccagacata ttccaatctt tctttttttc aagttcaaac    6600
aagctaaaag ggtttccatc ggcaatgact aaattatttg catatgttct tctaggtcct    6660
ggctaacgcc gataccctg atgatgcatt gactgcgcga acaatggggg cacaaggaat     6720
tggattatgc cggacagagc acatggtacg tccgatccta catagttttt ggctagggat    6780
acttggacat tttactcttc ctttagtttc tttgtcctag acaagaaaaa cagtttcatg    6840
ttttttctcc ccacctgtac ttggggcagt tctttgcttc agacgagagg attaaggctg    6900
tcaggcagat gattatggct cccacgcttg agctgaggca gcaggcgctc gaccgtctct    6960
tgccgtatca gaggtctgac ttcgaaggca ttttccgtgc tatggatggt aagtgaaaaa    7020
aacacagtgc atcccattta catgcaggac tgcatggtct gaacattctc ttggtatctt    7080
gcgtttcagg actcccggtg accatccgac tcctggaccc tcccctccac gagttccttc    7140
cagaagggaa catcgaggac attgtaagtg aattatgtgc tgagacggga gccaaccagg    7200
aggatgccct cgcgcgaatt gaaaagcttt cagaagtaaa cccgatgctt ggcttccgtg    7260
ggtgcaggtt ggatttctgc tactctatca cagcaaaaga aaaaaaaatc actggtgatg    7320
cctgattgac tgattttgga actgccgaaa tttccaggct tggtatatcg taccctgaat    7380
tgacagagat gcaagcccgg gccattttg aagctgctat agcaatgacc aaccaggtg     7440 ttcaagtgtt cccagagata atggttcctc ttgttggaac accacaggca tgtgtcttta   7500 cttttttatat attaatgtat gtacatactg tctctgcagt tcaaaaaaag tgagcaaata   7560
aatccagttg atgcagaaac aagcagctaa ttaatagctg acgtttggta tttccaggaa   7620
ctggggcatc aagtgactct tatccgccaa gttgctgaga agtgttcgc caatgtgggc     7680 aagactatcg ggtacaaagt tggaacaatg attgagatcc ccaggcagc tctggtggct     7740 gatgaggtag ggaaaactac caagttcaga atcgcccaga actttgccaa caagtttgtt   7800
tatctgtgca ttcctacgct ggtctgaaat ctgtggctgt tgttgttgtt ttttggtttt    7860
cgtcaacctg gcagatagcg gagcaggctg aattcttctc cttcggaacg aacgacctga    7920
cgcagatgac ctttgggtac agcagggatg atgtgggaaa gttcattccc gtctatcttg    7980
ctcagggcat tctccaacat gacccttcg aggtaactgt tgcaactctg cctgccaccc     8040
tcgcatgtcg catctgatgt gacatgagca tctcatgtcg cgatcgcctt tcatttggat    8100
gcccgtacac ctaccaggtc ctggaccaga ggggagtggg cgagctggtg aagcttgcta    8160
cagagagggg ccgcaaagct aggcctaact tgaaggttgg ttttgggaca ctgcttcgta    8220
cgtctcctta gaaaaccacg gtttgattgt tgtttggttt tgtgtgcaaa caggtgggca    8280
```

-continued

```
tttgtggaga acacggtgga gagccttcct ctgtggcctt cttcgcgaag gctgggctgg    8340
attacgtttc ttgctcccct ttcaggtcgg ttcagtcact gataaactcg tgattgaatc    8400
caataagcgt atcctcttat gttaacggta gcaaaatgtt cactgttttc tttgaatgct    8460
ttctgcaggg ttccgattgc taggctagct gcagctcagg tgcttgtctg aggctgcctc    8520
ctcattggca accggattgc ctgctgctgg tggatgtggt gatcaacagt attattacag    8580
agccatgcta tgtgaacatt actagtagca gtgctcataa aagctacaat cccatgtcct    8640
ttttttcccc agtcatgtaa aacttccaaa ctgctccatg gttcaaaact ctgttcttca    8700
atacatcatc aattatcgat tatatacgtg gcaagttttt ttctttgttt gcttttttc     8760 ctttctggca tgtgtttttt ggttttcttg gtgtgtgagg tgtgcatgtc gctaggatcc    8820
```

<210> SEQ ID NO 16
<211> LENGTH: 8820
<212> TYPE: DNA
<213> ORGANISM: maize
<220> FEATURE:
<223> OTHER INFORMATION: DNA sequence of mutated clone #2838 (promoter to terminator). Amino acid substituted maize genomic DNA

<400> SEQUENCE: 16

```
gaattcccat tttttgttgt tgtcaaaat aatcattgtt tggtcagtgg ttgttaggaa       60
ggaggtggat agaaagttaa atttagattt tccctggggt ggaggacatg aaagagtggg     120
aaaggttgct ggacattttg gaaggagtga taattactaa acgagaatat atgttatctt     180
cgtcgttaga gaaatctaga cagtatacaa caagatccac gtactatagg taaacttta     240 ggggtattgt gaacaagagg atgagtaaac tctaaaagaa caaagctcca atgaaaattt     300
aggtttttat gtggttagtc atagggcaag ttgcaaacag gtgttgatct aaaaaggaag    360
tagtagggaa atgtgaagtg tctttgcgag gaattggaaa atgaagatca cattttcttt    420
gggtgcatca tgggaagaac catttgggac tctttaagg aggcctaaga atgccataaa      480
gtttgcaaga tcttttgaa gagtgtctac ctataaacaa tagtaaatat catgtcaaat      540
ttttcatctt cgccattatt ctttaggaga atttagaatg ttccgaataa aatatggata    600
gaaaagaagt tcccaaagtc atccaatttt ctacaaaatc ttcaactta agattgagag      660 tgagtgttgt aaagttcttg gaagatgagt tgaacccat ggaggcgttg gctaaagtac      720
tgaaagcaat ctaaagacat ggaggtggaa ggcctgacgt agatagagaa gatgctctta    780
gctttcattg tctttctttt gtagtcatct gatttacctc tctcgtttat acaactggtt    840
ttttaaacac tccttaactt ttcaaattgt ctctttcttt accctagact agataatttt     900
aatggtgatt ttgctaatgt ggcgccatgt tagatagagg taaaatgaac tagttaaaag     960
ctcagagtga taaatcaggc tctcaaaaat tcataaactg ttttttaaat atccaaatat    1020
ttttacatgg aaaataataa aatttagttt agtattaaaa attcagttga atatagtttt    1080
gtcttcaaaa attatgaaac tgatcttaat tatttttcct taaaaccgtg ctctatcttt    1140
gatgtctagt ttgagacgat tgtataattt ttttgtgctt atctacgacg agctgaagta    1200
cgtagaaata ctagtggagt cgtgccgcgt gtgcctgtag ccactcgtac gctacagccc    1260
aagcgctaga gcccaagagg ccggaggtgg aaggcgtcgc ggcactatag ccactcgccg    1320
caagagccca agaggccgga gctggaagga tgagggtctg ggtgttcacg aattgcctgg    1380
aggcaggagg ctcgtcgtcc ggagccacag gcgtggagac gtccgggata aggtgagcag    1440
ccgctgcgat aggggcgcgt gtgaaccccg tcgcgcccca cggatggtat aagaataaag    1500
```

```
gcattccgcg tgcaggattc acccgttcgc ctctcacctt ttcgctgtac tcactcgcca   1560
cacacacccc ctctccagct ccgttggagc tccggacagc agcaggcgcg gggcggtcac   1620
gtagtaagca gctctcggct ccctctcccc ttgctccata tgatcgtgca acccatcgag   1680
ctacgcgcgt ggactgcctt ccctgggtcg gcgcaggagg ggatcggaag gatgacggca   1740
tcggtttcca gggccatctg cgtacagaag ccgggctcaa aatgcaccag ggacagggaa   1800
gcgacctcct tcgcccgccg atcggtcgca gcgccgaggc ccccgcacgc caaagccgcc   1860
ggcgtcatcc gctccgactc cggcgcggga cggggccagc attgctcgcc gctgagggcc   1920
gtcgttgacg ccgcgccgat acagacgacc aaaaaggtat cccttgcagc tcttagaaac   1980
tgaattctag aggttcaggg ttgtatatcc acaatctagt ttatccacca ttaataagat   2040
ataatttgtt acggcgtggc aatgcacttc cacgaactcc tgaggcagcg gataatgttt   2100
aaaaacgcat ttttgtcaac caggattaag aagctcattt tgagtttgcc cccatttggt   2160
tagaacatgg aaacgttct gcatatagtt ttcctctggg taagattgcg tagcgatcag    2220
gttttcggat cttccactcc gttttcccgt cgtcatacgt aggcgtagcg gtccacctca   2280
ttcgttcact tgtagttgta gctaggaagc tctctcccaa cggcgtgccg cacactcttt   2340
tgccggcccg acgcaaaaat ggcatgaatt tgctccaccg tgtttacata tgtaggagaa   2400
cttggataaa actgtgtaaa tactgcaaca catggatatg ggcactgtag tttaccctac   2460
cttaattaag caccaagctg cggcagagcg gctcggagtg cgtgcaaaaa cgacagccat   2520
ccgtgcgctc tccttgtggc ttctgcaggc tgcagcagct gccacccgcc cgcgccatgg   2580
acgcacggtg gacggtgctc tgcgcctctg cctatctccc gggaacgccg tgaccgggta   2640
ctagctagct tgaacgggat accaggcgga gacgcccgcg gatttgcgga agcgtatcgc   2700
cggccgtgct gcgatctata tcccatcgtc taacaggcga cccatccagc tgacgcgacg   2760
aattaacaac gctatccgcg cgcatgcatg gccatgactt ggctattttg cactgtgcaa   2820
atgtctgccc agtagttcat ctcacgaaca caaatgccgg tggtcagtag gagagagaag   2880
aactaactcc agcgtccgat cgggacgcca ctcgctcgct cacaagcaaa gacactagct   2940
agtctcaact ctcaactaca acaacgctag taaagcctaa aacacacaca cgcacgcaca   3000
cacaagcaaa gcgagcaacg tacgttcgtc agtgcgtcct tgtgaaacag aaagcgcgcg   3060
ctctagctat agctgcaccg tgtctgcatg cgtgctgaca cgacagggtg agtcacacag   3120
aagcggcgct tggacgctag cagcacgatc agttcagttt ttcagcgttt cttttttttt   3180
ctggctggat atgcatcacg catggaacaa gagggtgtga catgcacgcc cagtggtggt   3240
cgttcttgca ttgcatttgg gctctgtatg atttaagatg gagggagtag cacaagtgta   3300
gttggcaggc tatttaccga tgatcaattt ttattaccag gtactctatc aaacaagtag   3360
tagctctact gtttaattag tctaacaagt gtagttggca cgtagggaag caagcccatg   3420
ttgatctgag gtggccgcgg gcgtccggaa ctccggatat gtatgctcgc tgctaccggc   3480
cagtaagctg gggcatgcgt gcgttcactt gcttgagacc gtttctaact ttgcaaacaa   3540
aaaaaaaaca accagcacca gactacgtga cgtgtaaagc tcatcctgac tgtttattgc   3600
tgcctgtttg tgaagaaaga aagaaaaaaa aaagagaga gtcggccggg ctgctgcaca   3660
cgcacatcac tcgcggccgc cgctgctata aatagagccc ggggcaggcc ctgcttaatt   3720
catcaccagc cacggctgca tttatttgtc actgatcgtt gatcagccta gctagctagc   3780
gctgttttcc tgtgtgctaa tggcgcccgt tcaatgtgcg cgttcgcaga gggtgttcca   3840
```

```
cttcggcaag ggcaagagcg agggcaacaa gaccatgaag gaactggtga gaggtttctt    3900 cttttctgtat tctcgcttaa tctgcatgca tgcatgcata catactaatg aagtaataac   3960
gatgctgtcg atgaatgatg acgcatgcag ctgggcggca agggcgcgaa cctggcggag   4020
atggcgagca tcgggctgtc ggtgccgcca gggttcacgg tgtcgacgga ggcgtgccag   4080
cagtaccagg acgccgggtg cgccctcccc gcggggctct gggccgagat cgtcgacggc   4140
ctgcagtggg tggaggagta catgggcgcc accctgggcg atccgcagcg cccgctcctg   4200
ctctccgtcc gctccggcgc cgccgtgtcc atgcccggca tgatggacac ggtgctcaac   4260
ctggggctca acgacgaagt ggccgccggg ctggcggcca agagcgggga gcgcttcgcc   4320
tacgactcct tccgccgctt cctcgacatg ttcggcaacg tcgtgagtat ccccgcgcc    4380 gtagcatgcg tcttcgattc cgcgccctga ctcagctcct cgcttccatt cccgtccgcc   4440
ggttgttgtt actgctagct tgtcccacta gctaggtgca gtaggtgcct agttttgcgc   4500
gcatcgcgtc gcgtcgacga cgacccatcc tccaccgcgc tgccgtggcc gcaaccaagg   4560
ctggatggag cttttgtctg tttgccaggc cagccgttgc tttgggttaa aagtgcaaaa   4620
aaaaaatgat gaaggtcacg ctacgaacta aacagaccat atacgtacgg catcggcatg   4680
taaacttggc ttgtcggact cgagaaacga aagaacgatg actcaaactg ctctcagatt   4740
ttgtttcatt gtttgtgttt accaggtcat ggacatcccc cgctcactgt tcgaagagaa   4800
gcttgagcac atgaaggaat ccaaggggct gaagaacgac accgacctca cggcctctga   4860
cctcaaagag ctcgtgggtc agtacaagga ggtctacctc tcagccaagg gagagccatt   4920
cccctcaggt acataccggc ccgtcgatcg tcctcagctc tactgatcga tggagctagc   4980
ggtcagtttc cctgtgcacc gaaatcatgt gcttgcctgc cttgcagacc ccaagaagca   5040
gctggagcta gcagtgctgg ctgtgttcaa ctcgtgggag agccccaggg ccaagaagta   5100
caggagcatc aaccagatca ctggcctcag gggcaccgcc gtgaacgtgc agtgcatggt   5160
gttcggcaac atggggaaca cttctggcac cggcgtgctc ttcaccagga accccaacac   5220
cggagagaag aagctgtatg cgagttcct ggtgaacgct caggtatgag tcggccctca   5280
ggcttccatt gcgcgcctgt tcgtgcatgg atacacgtac gtacgttact tgacgccatg   5340
catgcaattc gtttcctgct cagggtgagg atgtggttgc cggaataaga accccagagg   5400
accttgacgc catgaagaac ctcatgccac aggcctacga cgagcttgtt gagaactgca   5460
acatcctgga gagccactac aaggaaatgc aggtacagtt taattttcac cttctaattt   5520
aaacaccaca ccaccgtctc tctctctctc tctggatcct gatgtttctt ctccagatga   5580
tgtgagctca ggctgagact tggtttttct ttggcgtgtg tgatcatgca ggatatcgag   5640
ttcactgtcc aggaaaacag gctgtggatg ttgcagtgca ggacagggaa acgtacgggc   5700
aaaagtgccg tgaagatcgc cgtggacatg ttaacgagg gccttgttga gccccgctca   5760
gcgatcaaga tggtagagcc aggccacctg gaccagcttc tccatcctca ggtaatctat   5820
cgatcaagaa ccatggacgt acgtactaag ggcttaccaa atcaatcctt actaatgccg   5880
ttatgcattg atgccgttat ggaaacccac agtttgagaa cccgtcggcg tacaaggatc   5940
aagtcattgc cactggtctg ccagcctcac ctggggctgc tgtgggccag ttgtgttca   6000 ctgctgagga tgctgaagca tggcattccc aagggaaagc tgctattctg gtaatattca   6060
tcgcaaaaca cttttattt ggactgcttt tccatacaac attttcacca gttttttgtaa   6120 atatatatac tgtatactgt atgcaggtaa gggcagagac cagccctgag gacgttggtg   6180
gcatgcacgc tgctgtgggg attcttacag agaggggtgg catgacttcc cacgctgctg   6240
```

```
tggtcgcacg tgggtggggg aaatgctgcg tctcgggatg ctcaggcatt cgcgtaaacg   6300
atgcggagaa ggtgacttga atcctctgt tacgcaagga agctccagca tgtctcgtga    6360
tttaccttgc tgtttattta tatgaattag ctcgtgacga tcggaggcca tgtgctgcgc   6420
gaaggtgagt ggctgtcgct gaatgggtcg actggtgagg tgatccttgg gaagcagccg   6480 cttccccac cagcccttag tggtgatctg ggaactttca tggcctgggt ggatgatgtt    6540
agaaagctca aggtaaaaat cccagacata ttccaatctt tctttttttc aagttcaaac   6600
aagctaaaag ggtttccatc ggcaatgact aaattatttg catatgttct tctaggtcct   6660
ggctaacgcc gatacccctg atgatgcatt gactgcgcga acaatggggg cacaaggaat   6720
tggattatgc cggacagagc acatggtacg tccgatccta catagttttt ggctagggat   6780
acttggacat tttactcttc ctttagtttc tttgtcctag acaagaaaaa cagtttcatg   6840
ttttttctcc ccacctgtac ttggggcagt tctttgcttc agacgagagg attaaggctg   6900
tcaggcagat gattatggct cccacgcttg agctgaggca gcaggcgctc gaccgtctct   6960
tgccgtatca gaggtctgac ttcgaaggca ttttccgtgc tatggatggt aagtgaaaaa   7020
aacacagtgc atcccattta catgcaggac tgcatggtct gaacattctc ttggtatctt   7080
gcgtttcagg actcccggtg accatccgac tcctggaccc tcccctccac gagttccttc   7140
cagaagggaa catcgaggac attgtaagtg aattatgtgc tgagacggga gccaaccagg   7200
aggatgccct cgcgcgaatt gaaaagcttt cagaagtaaa cccgatgctt ggcttccgtg   7260
ggtgcaggtt ggatttctgc tactctatca cagcaaaaga aaaaaaaatc actggtgatg   7320
cctgattgac tgattttgga actgccgaaa tttccaggct tggtatatcg taccctgaat   7380
tgacagagat gcaagcccgg gccattttg aagctgctat agcaatgacc aaccaggtg     7440 ttcaagtgtt cccagagata atggttcctc ttgttggaac accacaggca tgtgtcttta   7500 cttttttatat attaatgtat gtacatactg tctctgcagt tcaaaaaaag tgagcaaata   7560
aatccagttg atgcagaaac aagcagctaa ttaatagctg acgtttggta tttccaggaa   7620
ctggggcatc aagtgactct tatccgccaa ggttgctgaga aagtgttcgc caatgtgggc  7680
aagactatcg ggtacaaagt tggaacaatg attgagatcc ctcgagcagc tctgatcgct   7740
gatgaggtag ggaaaactac caagttcaga atcgcccaga actttgccaa caagtttgtt   7800
tatctgtgca ttcctacgct ggtctgaaat ctgtggctgt tgttgttgtt tttttggttt   7860
cgtcaacctg gcagatagcg aaggaggctg aattcttctc cttcggaacg aacgacctga   7920
cgcagatgac ctttgggtac agcagggatg atgtgggaaa gttccttccc atctatcttt   7980
cccagggcat tctccaacat gacccctccg aggtaactgt tgcaactctg cctgccaccc   8040
tcgcatgtcg catctgatgt gacatgagca tctcatgtcg cgatcgcctt tcatttggat   8100
gcccgtacac ctaccaggtc ctggaccaga agggagtggg ccagctgatc aagatggcta   8160
cagagaaggg ccgcgccgct aaccctaact tgaaggttgg ttttgggaca ctgcttcgta   8220
cgtctcctta gaaaccacg gtttgattgt tgtttggttt tgtgtgcaaa caggtgggca    8280
tttgtggaga acacggtgga gagccttcct ctgtggcctt cttcgacggg gttgggctgg   8340
attacgtttc ttgctcccct ttcaggtcgg ttcagtcact gataaactcg tgattgaatc   8400
caataagcgt atcctcttat gttaacggta gcaaaatgtt cactgttttc tttgaatgct   8460
ttctgcaggg ttccgattgc taggctagct gcagctcagg tggttgtctg aggctgcctc   8520
ctcattggca accggattgc ctgctgctgg tggatgtggt gatcaacagt attattacag   8580
```

```
agccatgcta tgtgaacatt actagtagca gtgctcataa aagctacaat cccatgtcct    8640
tttttttccc agtcatgtaa aacttccaaa ctgctccatg gttcaaaact ctgttcttca    8700
atacatcatc aattatcgat tatatacgtg gcaagttttt ttctttgttt gcttttttc    8760 ctttctggca tgtgtttttt ggttttcttg gtgtgtgagg tgtgcatgtc gctaggatcc    8820
```

<210> SEQ ID NO 17
<211> LENGTH: 947
<212> TYPE: PRT
<213> ORGANISM: maize
<220> FEATURE:
<223> OTHER INFORMATION: PPDK

<400> SEQUENCE: 17

```
Met Thr Ala Ser Val Ser Arg Ala Ile Cys Val Gln Lys Pro Gly Ser
1               5                   10                  15

Lys Cys Thr Arg Asp Arg Glu Ala Thr Ser Phe Ala Arg Arg Ser Val
            20                  25                  30

Ala Ala Pro Arg Pro His Ala Lys Ala Gly Val Ile Arg Ser
        35                  40                  45

Asp Ser Gly Ala Gly Arg Gly Gln His Cys Ser Pro Leu Arg Ala Val
    50                  55                  60

Val Asp Ala Ala Pro Ile Gln Thr Thr Lys Lys Arg Val Phe His Phe
65                  70                  75                  80

Gly Lys Gly Lys Ser Glu Gly Asn Lys Thr Met Lys Glu Leu Leu Gly
                85                  90                  95

Gly Lys Gly Ala Asn Leu Ala Glu Met Ala Ser Ile Gly Leu Ser Val
            100                 105                 110

Pro Pro Gly Phe Thr Val Ser Thr Glu Ala Cys Gln Gln Tyr Gln Asp
        115                 120                 125

Ala Gly Cys Ala Leu Pro Ala Gly Leu Trp Ala Glu Ile Val Asp Gly
    130                 135                 140

Leu Gln Trp Val Glu Glu Tyr Met Gly Ala Thr Leu Gly Asp Pro Gln
145                 150                 155                 160

Arg Pro Leu Leu Leu Ser Val Arg Ser Gly Ala Ala Val Ser Met Pro
                165                 170                 175

Gly Met Met Asp Thr Val Leu Asn Leu Gly Leu Asn Asp Glu Val Ala
            180                 185                 190

Ala Gly Leu Ala Ala Lys Ser Gly Glu Arg Phe Ala Tyr Asp Ser Phe
        195                 200                 205

Arg Arg Phe Leu Asp Met Phe Gly Asn Val Val Met Asp Ile Pro Arg
    210                 215                 220

Ser Leu Phe Glu Glu Lys Leu Glu His Met Lys Glu Ser Lys Gly Leu
225                 230                 235                 240

Lys Asn Asp Thr Asp Leu Thr Ala Ser Asp Leu Lys Glu Leu Val Gly
                245                 250                 255

Gln Tyr Lys Glu Val Tyr Leu Ser Ala Lys Gly Glu Pro Phe Pro Ser
            260                 265                 270

Asp Pro Lys Lys Gln Leu Glu Leu Ala Val Leu Ala Val Phe Asn Ser
        275                 280                 285

Trp Glu Ser Pro Arg Ala Lys Lys Tyr Arg Ser Ile Asn Gln Ile Thr
    290                 295                 300

Gly Leu Arg Gly Thr Ala Val Asn Val Gln Cys Met Val Phe Gly Asn
305                 310                 315                 320

Met Gly Asn Thr Ser Gly Thr Gly Val Leu Phe Thr Arg Asn Pro Asn
```

-continued

```
                325                 330                 335
Thr Gly Glu Lys Lys Leu Tyr Gly Glu Phe Leu Val Asn Ala Gln Gly
            340                 345                 350
Glu Asp Val Val Ala Gly Ile Arg Thr Pro Glu Asp Leu Asp Ala Met
            355                 360                 365
Lys Asn Leu Met Pro Gln Ala Tyr Asp Glu Leu Val Glu Asn Cys Asn
            370                 375                 380
Ile Leu Glu Ser His Tyr Lys Glu Met Gln Asp Ile Glu Phe Thr Val
385                 390                 395                 400
Gln Glu Asn Arg Leu Trp Met Leu Gln Cys Arg Thr Gly Lys Arg Thr
            405                 410                 415
Gly Lys Ser Ala Val Lys Ile Ala Val Asp Met Val Asn Glu Gly Leu
            420                 425                 430
Val Glu Pro Arg Ser Ala Ile Lys Met Val Glu Pro Gly His Leu Asp
            435                 440                 445
Gln Leu His Pro Gln Phe Glu Asn Pro Ser Ala Tyr Lys Asp Gln
            450                 455                 460
Val Ile Ala Thr Gly Leu Pro Ala Ser Pro Gly Ala Ala Val Gly Gln
465                 470                 475                 480
Val Val Phe Thr Ala Glu Asp Ala Glu Ala Trp His Ser Gln Gly Lys
            485                 490                 495
Ala Ala Ile Leu Val Arg Ala Glu Thr Ser Pro Glu Asp Val Gly Gly
            500                 505                 510
Met His Ala Ala Val Gly Ile Leu Thr Glu Arg Gly Gly Met Thr Ser
            515                 520                 525
His Ala Ala Val Ala Arg Gly Trp Gly Lys Cys Cys Val Ser Gly
            530                 535                 540
Cys Ser Gly Ile Arg Val Asn Asp Ala Glu Lys Leu Val Thr Ile Gly
545                 550                 555                 560
Gly His Val Leu Arg Glu Gly Glu Trp Leu Ser Leu Asn Gly Ser Thr
            565                 570                 575
Gly Glu Val Ile Leu Gly Lys Gln Pro Leu Ser Pro Pro Ala Leu Ser
            580                 585                 590
Gly Asp Leu Gly Thr Phe Met Ala Trp Val Asp Asp Val Arg Lys Leu
            595                 600                 605
Lys Val Leu Ala Asn Ala Asp Thr Pro Asp Asp Ala Leu Thr Ala Arg
            610                 615                 620
Asn Asn Gly Ala Gln Gly Ile Gly Leu Cys Arg Thr Glu His Met Phe
625                 630                 635                 640
Phe Ala Ser Asp Glu Arg Ile Lys Ala Val Arg Gln Met Ile Met Ala
            645                 650                 655
Pro Thr Leu Glu Leu Arg Gln Gln Ala Leu Asp Arg Leu Leu Pro Tyr
            660                 665                 670
Gln Arg Ser Asp Phe Glu Gly Ile Phe Arg Ala Met Asp Gly Leu Pro
            675                 680                 685
Val Thr Ile Arg Leu Leu Asp Pro Pro Leu His Glu Phe Leu Pro Glu
            690                 695                 700
Gly Asn Ile Glu Asp Ile Val Ser Glu Leu Cys Ala Glu Thr Gly Ala
705                 710                 715                 720
Asn Gln Glu Asp Ala Leu Ala Arg Ile Glu Lys Leu Ser Glu Val Asn
            725                 730                 735
Pro Met Leu Gly Phe Arg Gly Cys Arg Leu Gly Ile Ser Tyr Pro Glu
            740                 745                 750
```

Leu Thr Glu Met Gln Ala Arg Ala Ile Phe Glu Ala Ile Ala Met
        755                 760                 765

Thr Asn Gln Gly Val Gln Val Phe Pro Glu Ile Met Val Pro Leu Val
    770                 775                 780

Gly Thr Pro Gln Glu Leu Gly His Gln Val Thr Leu Ile Arg Gln Val
785                 790                 795                 800

Ala Glu Lys Val Phe Ala Asn Val Gly Lys Thr Ile Gly Tyr Lys Val
                805                 810                 815

Gly Thr Met Ile Glu Ile Pro Arg Ala Ala Leu Val Ala Asp Glu Ile
            820                 825                 830

Ala Glu Gln Ala Glu Phe Phe Ser Phe Gly Thr Asn Asp Leu Thr Gln
        835                 840                 845

Met Thr Phe Gly Tyr Ser Arg Asp Asp Val Gly Lys Phe Ile Pro Val
    850                 855                 860

Tyr Leu Ala Gln Gly Ile Leu Gln His Asp Pro Phe Glu Val Leu Asp
865                 870                 875                 880

Gln Arg Gly Val Gly Glu Leu Val Lys Leu Ala Thr Glu Arg Gly Arg
                885                 890                 895

Lys Ala Arg Pro Asn Leu Lys Val Gly Ile Cys Gly Glu His Gly Gly
            900                 905                 910

Glu Pro Ser Ser Val Ala Phe Phe Ala Lys Ala Gly Leu Asp Tyr Val
        915                 920                 925

Ser Cys Ser Pro Phe Arg Val Pro Ile Ala Arg Leu Ala Ala Ala Gln
    930                 935                 940

Val Leu Val
945     947

<210> SEQ ID NO 18
<211> LENGTH: 955
<212> TYPE: PRT
<213> ORGANISM: Flaveria brownii
<220> FEATURE:
<223> OTHER INFORMATION: PPDK

<400> SEQUENCE: 18

Met Ser Ser Leu Phe Val Glu Gly Met Pro Leu Lys Ser Ala Asn Glu
1               5                   10                  15

Ser Cys Leu Pro Ala Ser Val Lys Gln Arg Arg Thr Gly Asp Leu Arg
                20                  25                  30

Arg Leu Asn His His Arg Gln Pro Ala Phe Val Arg Gly Ile Cys Arg
            35                  40                  45

Arg Lys Leu Ser Gly Val Ser Arg Ile Glu Leu Arg Thr Gly Gly Leu
        50                  55                  60

Thr Leu Pro Arg Ala Val Leu Asn Pro Val Ser Pro Val Thr Thr
65                  70                  75                  80

Thr Lys Lys Arg Val Phe Thr Phe Gly Lys Gly Asn Ser Glu Gly Asn
                85                  90                  95

Lys Asp Met Lys Ser Leu Leu Gly Gly Lys Gly Ala Asn Leu Ala Glu
            100                 105                 110

Met Ala Ser Ile Gly Leu Ser Val Pro Pro Gly Leu Thr Ile Ser Thr
        115                 120                 125

Glu Ala Cys Glu Glu Tyr Gln Gln Asn Gly Lys Lys Leu Pro Pro Gly
    130                 135                 140

Leu Trp Asp Glu Ile Leu Glu Gly Leu Gln Tyr Val Gln Lys Glu Met
145                 150                 155                 160

-continued

```
Ser Ala Ser Leu Gly Asp Pro Ser Lys Ala Leu Leu Ser Val Arg
                165                 170                 175

Ser Gly Ala Ala Ile Ser Met Pro Gly Met Met Asp Thr Val Leu Asn
            180                 185                 190

Leu Gly Leu Asn Asp Glu Val Val Asp Gly Leu Ala Ala Lys Ser Gly
        195                 200                 205

Ala Arg Phe Ala Tyr Asp Ser Tyr Arg Arg Phe Leu Asp Met Phe Gly
    210                 215                 220

Asn Val Val Met Gly Ile Pro His Ser Leu Phe Asp Glu Lys Leu Glu
225                 230                 235                 240

Gln Met Lys Ala Glu Lys Gly Ile His Leu Asp Thr Asp Leu Thr Ala
                245                 250                 255

Ala Asp Leu Lys Asp Leu Ala Glu Gln Tyr Lys Asn Val Tyr Val Glu
            260                 265                 270

Ala Lys Gly Glu Lys Phe Pro Thr Asp Pro Lys Lys Gln Leu Glu Leu
        275                 280                 285

Ala Val Asn Ala Val Phe Asp Ser Trp Asp Ser Pro Arg Ala Asn Lys
    290                 295                 300

Tyr Arg Ser Ile Asn Gln Ile Thr Gly Leu Lys Gly Thr Ala Val Asn
305                 310                 315                 320

Ile Gln Cys Met Val Phe Gly Asn Met Gly Asn Thr Ser Gly Thr Gly
                325                 330                 335

Val Leu Phe Thr Arg Asn Pro Ser Thr Gly Glu Lys Lys Leu Tyr Gly
            340                 345                 350

Glu Phe Leu Val Asn Ala Gln Gly Glu Asp Val Val Ala Gly Ile Arg
        355                 360                 365

Thr Pro Glu Asp Leu Val Thr Met Glu Thr Cys Met Pro Glu Ala Tyr
    370                 375                 380

Arg Glu Leu Val Glu Asn Cys Val Ile Leu Glu Arg His Tyr Lys Asp
385                 390                 395                 400

Met Met Asp Ile Glu Phe Thr Val Gln Glu Asn Arg Leu Trp Met Leu
                405                 410                 415

Gln Cys Arg Thr Gly Lys Arg Thr Gly Lys Gly Ala Val Arg Ile Ala
            420                 425                 430

Val Asp Met Val Asn Glu Gly Leu Ile Asp Thr Arg Thr Ala Ile Lys
        435                 440                 445

Arg Val Glu Thr Gln His Leu Asp Gln Leu Leu His Pro Gln Phe Glu
    450                 455                 460

Asn Pro Ser Ala Tyr Lys Ser His Val Val Ala Thr Gly Leu Pro Ala
465                 470                 475                 480

Ser Pro Gly Ala Ala Val Gly Gln Val Val Phe Ser Ala Glu Asp Ala
                485                 490                 495

Glu Thr Trp His Ala Gln Gly Lys Ser Ala Ile Leu Val Arg Thr Glu
            500                 505                 510

Thr Ser Pro Glu Asp Val Gly Gly Met His Ala Ala Gly Ile Leu
        515                 520                 525

Thr Ala Arg Gly Gly Met Thr Ser His Ala Ala Val Val Ala Arg Gly
    530                 535                 540

Trp Gly Lys Cys Cys Val Ser Gly Cys Ala Asp Ile Arg Val Asn Asp
545                 550                 555                 560

Asp Met Lys Val Phe Thr Ile Gly Asp Arg Val Ile Lys Glu Gly Asp
                565                 570                 575
```

```
Trp Leu Ser Leu Asn Gly Ser Thr Gly Glu Val Ile Leu Gly Lys Gln
            580                 585                 590

Leu Leu Ala Pro Pro Ala Met Ser Asn Asp Leu Glu Thr Phe Met Ser
        595                 600                 605

Trp Ala Asp Gln Ala Arg Arg Leu Lys Val Met Ala Asn Ala Asp Thr
    610                 615                 620

Pro Asn Asp Ala Leu Thr Ala Arg Asn Asn Gly Ala Gln Gly Ile Gly
625                 630                 635                 640

Leu Cys Arg Thr Glu His Met Phe Phe Ala Ser Asp Glu Arg Ile Lys
                645                 650                 655

Ala Val Arg Lys Met Ile Met Ala Val Thr Pro Glu Gln Arg Lys Ala
            660                 665                 670

Ala Leu Asp Leu Leu Leu Pro Tyr Gln Arg Ser Asp Phe Glu Gly Ile
        675                 680                 685

Phe Arg Ala Met Asp Gly Leu Pro Val Thr Ile Arg Leu Leu Asp Pro
    690                 695                 700

Pro Leu His Glu Phe Leu Pro Glu Gly Asp Leu Glu His Ile Val Asn
705                 710                 715                 720

Glu Leu Thr Ala Asp Thr Gly Met Ser Lys Asp Glu Ile Tyr Ser Arg
                725                 730                 735

Ile Glu Lys Leu Ser Glu Val Asn Pro Met Leu Gly Phe Arg Gly Cys
            740                 745                 750

Arg Leu Gly Ile Ser Tyr Pro Glu Leu Thr Glu Met Gln Val Arg Ala
        755                 760                 765

Ile Phe Gln Ala Ala Val Ser Met Asn Asn Gln Gly Val Thr Val Ile
    770                 775                 780

Pro Glu Ile Met Val Pro Leu Val Gly Thr Pro Gln Glu Leu Arg His
785                 790                 795                 800

Gln Ile Gly Val Ile Arg Gly Val Ala Ala Asn Val Phe Ala Glu Met
                805                 810                 815

Gly Leu Thr Leu Glu Tyr Lys Val Gly Thr Met Ile Glu Ile Pro Arg
            820                 825                 830

Ala Ala Leu Ile Ala Asp Glu Ile Ala Lys Glu Ala Gly Phe Phe Ser
        835                 840                 845

Phe Gly Thr Asn Asp Leu Thr Gln Met Thr Phe Gly Tyr Ser Arg Asp
    850                 855                 860

Asp Val Gly Lys Phe Leu Pro Ile Tyr Leu Ser Gln Gly Ile Leu Gln
865                 870                 875                 880

His Asp Pro Phe Glu Val Leu Asp Gln Lys Gly Val Gly Gln Leu Ile
                885                 890                 895

Lys Met Ala Thr Glu Lys Gly Arg Ala Ala Asn Pro Asn Leu Lys Val
            900                 905                 910

Gly Ile Cys Gly Glu His Gly Gly Glu Pro Ser Ser Val Ala Phe Phe
        915                 920                 925

Asp Gly Val Gly Leu Asp Tyr Val Ser Cys Ser Pro Phe Arg Val Pro
    930                 935                 940

Ile Ala Arg Leu Ala Ala Ala Gln Val Val Val
945                 950                 955

<210> SEQ ID NO 19
<211> LENGTH: 827
<212> TYPE: DNA
<213> ORGANISM: maize
<220> FEATURE:
<223> OTHER INFORMATION: DNA consisting of a nucleotide sequence
```

-continued corresponding to the 1/6 region of amino acid substituted PPDK
(Nos.7682- substituted maize genomic DNA.

<400> SEQUENCE: 19

```
agactatcgg gtacaaagtt ggaacaatga ttgagatccc tcgagcagct ctgatcgctg      60
atgaggtagg gaaaactacc aagttcagaa tcgcccagaa ctttgccaac aagtttgttt     120
atctgtgcat tcctacgctg gtctgaaatc tgtggctgtt gttgttgttt ttttggtttc     180
gtcaacctgg cagatagcga aggaggctga attcttctcc ttcggaacga acgacctgac     240
gcagatgacc tttgggtaca gcagggatga tgtgggaaag ttccttccca tctatctttc     300
ccagggcatt ctccaacatg accccttcga ggtaactgtt gcaactctgc ctgccaccct     360
cgcatgtcgc atctgatgtg acatgagcat ctcatgtcgc gatcgccttt catttggatg     420
cccgtacacc taccaggtcc tggaccagaa gggagtgggc cagctgatca agatggctac     480
agagaagggc cgcgccgcta accctaactt gaaggttggt tttgggacac tgcttcgtac     540
gtctccttag aaaaccacgg tttgattgtt gtttggtttt gtgtgcaaac aggtgggcat     600
ttgtggagaa cacggtggag agccttcctc tgtggccttc ttcgacgggg ttgggctgga     660
ttacgtttct tgctcccctt tcaggtcggt tcagtcactg ataaactcgt gattgaatcc     720
aataagcgta tcctcttatg ttaacggtag caaaatgttc actgttttct ttgaatgctt     780
tctgcagggt tccgattgct aggctagctg cagctcaggt ggttgtc                   827
```